(12) United States Patent
Dai et al.

(10) Patent No.: US 11,177,019 B2
(45) Date of Patent: Nov. 16, 2021

(54) METHOD FOR BIOLOGICALLY STORING AND RESTORING DATA

(71) Applicant: Tsinghua University, Beijing (CN)

(72) Inventors: Junbiao Dai, Beijing (CN); Qingyu Wu, Beijing (CN); Naigemaiti Yijiati, Beijing (CN); Kaiwen Sun, Beijing (CN); Junkai Dong, Beijing (CN); Yiran Qin, Beijing (CN)

(73) Assignee: Tsinghua University, Beijing (CN)

( * ) Notice: Subject to any disclaimer, the term of this patent is extended or adjusted under 35 U.S.C. 154(b) by 338 days.

(21) Appl. No.: 16/328,745

(22) PCT Filed: Aug. 30, 2016

(86) PCT No.: PCT/CN2016/097398
§ 371 (c)(1),
(2) Date: Feb. 27, 2019

(87) PCT Pub. No.: WO2018/039938
PCT Pub. Date: Mar. 8, 2018

(65) Prior Publication Data
US 2019/0311782 A1 Oct. 10, 2019

(51) Int. Cl.
*G16B 30/00* (2019.01)
*G06F 16/25* (2019.01)
*G06N 3/12* (2006.01)

(52) U.S. Cl.
CPC .......... *G16B 30/00* (2019.02); *G06F 16/258* (2019.01); *G06N 3/12* (2013.01)

(58) Field of Classification Search
CPC ........ G16B 30/00; G16B 50/00; G16B 50/40; G16B 50/30; G06N 3/123; G06N 3/002; G06N 3/12; H03M 13/00; H03M 13/05; G06F 16/258
See application file for complete search history.

(56) References Cited

U.S. PATENT DOCUMENTS

| | | | |
|---|---|---|---|
| 8,412,462 B1* | 4/2013 | Ganeshalingam | G16B 50/00 702/19 |
| 10,930,370 B2* | 2/2021 | Strauss | C12Q 1/6869 |
| 2004/0086861 A1* | 5/2004 | Omori | H03M 13/00 435/6.14 |
| 2016/0180019 A1* | 6/2016 | Van Rooyen | G16B 40/00 702/19 |
| 2016/0306923 A1* | 10/2016 | van Rooyen | G06F 12/0877 |
| 2017/0141793 A1* | 5/2017 | Strauss | H03M 13/373 |
| 2018/0211001 A1* | 7/2018 | Gopalan | G16B 30/00 |

(Continued)

*Primary Examiner* — Shean Tokuta
(74) *Attorney, Agent, or Firm* — Wiggin and Dana LLP; Gregory S. Rosenblatt; Rikesh P. Patel

(57) ABSTRACT

The present invention relates to a method, device and software product for converting data into a data DNA sequence and restoring the DNA sequence library into raw data, and a storage medium for storing the software product. The method for converting data into a data DNA sequence comprises: dividing data into one or more data conversion units, providing a binary sequence for each data conversion unit, and converting each data conversion unit into a data DNA sequence according to a dataDNA sequence conversion rule, thus acquiring a data DNA sequence library, which makes biological storage of data in vivo possible by constructing a data DNA library.

20 Claims, 6 Drawing Sheets
Specification includes a Sequence Listing.

(56) References Cited

U.S. PATENT DOCUMENTS

| | | | |
|---|---|---|---|
| 2018/0253563 A1* | 9/2018 | Peck | G16B 50/00 |
| 2019/0020353 A1* | 1/2019 | Erlich | H03M 7/70 |
| 2019/0089372 A1* | 3/2019 | Roth | H04L 9/3218 |
| 2019/0136307 A1* | 5/2019 | Predki | C12P 19/34 |
| 2019/0355442 A1* | 11/2019 | Merriman | C12Q 1/6869 |
| 2020/0035331 A1* | 1/2020 | Milenkovic | B01J 19/0046 |
| 2020/0185057 A1* | 6/2020 | Leake | C12Q 1/6869 |
| 2020/0201812 A1* | 6/2020 | Unidad | C12Q 1/68 |
| 2020/0217813 A1* | 7/2020 | Merriman | G01N 33/48721 |
| 2020/0242482 A1* | 7/2020 | Merriman | G16B 30/20 |
| 2021/0074380 A1* | 3/2021 | Yekhanin | G06F 11/085 |

* cited by examiner

Figure 11

METHOD FOR BIOLOGICALLY STORING AND RESTORING DATA

TECHNICAL FIELD

The present invention relates to the fields of bioinformatics, synthetic biology and computers, and particularly relates to a conversion method capable of converting data into DNA sequences with biocompatibility and restoring a DNA sequence library to raw data.

BACKGROUND

The 21st century is a century of life sciences and a century of information and big data. Currently, the information technology is booming, and an important issue associated is how to deal with the increasingly growing data. According to the information provided by the International Data Corporation, the total amount of information data generated worldwide in 2009 had reached approximately 0.8 ZB (1 ZB=$1.18*10^{21}$B) in 2009. Also, the agency predicts that by 2020, the total amount of global data will reach 40 ZB. The existing data storage technologies have exposed their deficiencies in storage of such a large amount of data, such as low density, high energy consumption, and short period. There is a growing need for new ways to solve the problem of data storage. Under this realistic background, DNA, a bio-macromolecule that has long been responsible for the storage of genetic information, has gradually attracted the attention of scientists. As the carrier of genetic information, DNA has a data storage density far beyond the existing storage technologies, and can maintain the integrity of stored information in a sub-optimal environment; and DNA has a long life cycle and allows information to be copied by self-replicating or artificial amplification.

Previous efforts in the use of DNA information storage technology to achieve biological storage of data have been attempted. For example, through "fragmentation" of data DNA and ASCII based binary number conversion, Church et al. changed the thinking from the original research where all data was converted to a complete long single-stranded DNA to using a series of partially overlapping short DNA sequences (the complete set of sequences represents complete data information) for data storage. On this basis, Goldman et al. further optimized the strategy, that is, improving the information storage rate by using a ternary conversion algorithm, preventing the repeated occurrence of single bases by "free bases", and increasing the copying of data DNA by a quadruple redundancy mechanism generated by partially overlapping short sequences, to prevent errors in DNA synthesis, storage, and sequencing. Church and Goldman, et al. believed that the data DNA obtained should be stored in vitro, and the transfer of data DNA into a biological carrier does not have any economic benefits, but causes many problems instead. It was David Haughton et al. who actually realized the storage of artificially synthetic data DNA in a biological carrier, and they achieved prevention of foreign DNA from significantly influencing the activities of carrier organisms and also prevention of the passaging process of carrier organisms from introducing mutations into the data DNA sequences by means such as integrating data DNA into useless regions in the noncoding DNA sequences of carrier cells, the "quaternary-like" algorithm that achieves high information storage rate while preventing the occurrence of initiation codon, LDPC codes plus+modified watermark synchronization code that solve the resynchronization and error correction after gene mutation.

Although previous studies have made great progress in using DNA to store data, there are still many problems. First, the binary algorithm adopted by Church et al. has a large room for improvement in information storage density, and the problem of higher mutation rate introduced by continuous repetition of single bases has not been solved. Second, although the team led by Goldman had some improvement in both of the above problems by applying the ternary algorithm, the information storage density of the 2.2 PB/g single-stranded DNA obtained by them is still far from the theoretical value of 445 EB/g single-stranded DNA, which arises from the limitation of the ternary conversion algorithm itself, as well as the fact that the quadruple redundancy error correction mechanism increases the length of sequence to four times of the original one, reduces the conversion efficiency to a quarter and accordingly increases the cost of DNA synthesis and sequencing by four times; moreover, Church and Goldman, et al. have only solved the problem of storing data by DNA in vitro, but didn't provide proper solutions for the biocompatibility and error correction mechanisms needed in implanting data DNA into biological organisms; finally, David Haughton et al. from the computer field have realized significant improvement in information storage intensity by combining the "quaternary-like" algorithm and the channel coding technology, and gave a near optimal solution that meets the needs of biocompatibility and error correction mechanism. However, problems still exist. For example, in the "quaternary-like" algorithm, the problem that bit 1 or 2 at the end of a 0/1 binary number sequence cannot be correctly encoded, and the problem of the occurrence of an initiation codon during the generation and integration of the position information sequences, may occur. In addition, David Haughton et al. only provided a solution of how to convert the data into data DNA sequences, while for the complete process of biological storage, they neither provided any solution, nor carried out any practical trail or test.

SUMMARY OF THE INVENTION

The present invention discloses a method for converting data into data DNA sequences used as an information storage medium to store data. The DNA sequences obtained using the method of the present invention are suitable for being stored in organisms, for example, stored in cells in the form of plasmids, or integrated into cell genomes.

In the method of the present invention, data having a large amount of information is divided into data conversion units, each data conversion unit is converted into a single-stranded DNA short sequence, and therefore the data is converted into a set of single-stranded DNA short sequences. The length of each single-stranded DNA short sequence makes it appropriate for genetic manipulation. For example, it is appropriate for being cloned into a plasmid or for being integrated into a cell genome, thereby facilitating storage of the converted DNA sequences in an organism.

In the present invention, a specially designed dataDNA sequence conversion rule is used to convert a data conversion unit into a dataDNA sequence representing the data information of the conversion unit, and to restore a dataDNA sequence in the single-stranded DNA short sequence to a binary number sequence of the data conversion unit. The dataDNA sequence conversion rule prevents the generation of an initiation codon in the dataDNA sequence and prevents the generation of a continuously repeated single-base sequence in the data DNA sequence. The dataDNA sequence conversion rule is:

(a) for the i-th position in the dataDNA sequence, the two bases before this position are represented as d=[i−2, i−1];

(b) for the first two positions in the dataDNA sequence, the corresponding conversion between binary numbers and bases is performed according to the correspondence corresponding with the condition d∉Set {AT, CT, TT, CA, AA, GG CC} shown in the table below;

| | Correspondence | |
|---|---|---|
| Conditions | Binary numbers | Bases |
| d = [A, T] | 0, 10, 11 | A, T, C |
| d = [C, T] | 0, 10, 11 | A, T, C |
| d = [T, T] | 0, 1 | A, C |
| d = [C, A]* | — | C |
| d = [A, A] | 0, 10, 11 | T, C, G |
| d = [G, G] | 0, 10, 11 | A, T, C |
| d = [C, C] | 0, 10, 11 | A, T, G |
| d ∉ Set{AT, CT, TT, CA, AA, GG, CC} | 00, 01, 10, 11 | A, T, C, G |

*wherein when d = [C, A], base C is at the i-th position, and the base C does not correspond to any binary number (c) starting from the third position in the dataDNA sequence, the conversion is conducted sequentially according to the rules shown in above table by: first, judging which condition in the table the i-th position satisfies, and then performing the corresponding conversion between the binary number and the base at the i-th position according to the correspondence corresponding with the condition;

(d) when the binary number sequence has only 1 or 2 positions left, the conversion between binary numbers and bases is performed using the rules shown in the table below.

| | Bases | | | | | |
|---|---|---|---|---|---|---|
| | AC | TC | CG | GA | GT | GC |
| Binary number sequences | 0 | 1 | 00 | 01 | 10 | 11 |

Unless otherwise specified, the "dataDNA sequence conversion rule" mentioned in any of the solutions described below refers to the above dataDNA sequence conversion rule.

In the present invention, each single-stranded DNA short sequence may further comprise an indexDNA sequence representing positional information of the data conversion unit to indicate the positional information of the data conversion unit contained in the single-stranded DNA short sequence in the entire data, thereby facilitating the splicing of these data conversion units into raw data when a set of a series of single-stranded DNA short sequences is restored to a series of data conversion units. In the present invention, when an indexDNA sequence is to be obtained, the position number of the data conversion unit in the data is first converted into a ternary number sequence with a fixed number of bits, and then the ternary number sequence is converted into an indexDNA sequence according to a specially designed indexDNA sequence conversion rule, wherein the number of bases of the indexDNA sequence is the same as the number of bits of the ternary number sequence. When data is restored, the indexDNA sequence is first converted into a ternary number sequence using the indexDNA sequence conversion rule, and then the ternary number sequence is converted into the position number of the data conversion unit in the data. The indexDNA sequence conversion rule is:

(a) for the i-th position in the indexDNA sequence, the two bases before this position are represented as d=[i−2, i−1];

(b) for the first two positions in the indexDNA sequence, the corresponding conversion between ternary numbers and bases is performed according to the correspondence corresponding with the condition d∉Set {AT,CT,TT,CA,AA,CC,GG} shown in the table below;

| | Correspondence | |
|---|---|---|
| Conditions | Ternary numbers | Bases |
| d = [A, T] | 0, 1, 2 | A, T, C |
| d = [C, T] | 0, 1, 2 | A, T, C |
| d = [T, T] | 0, 1, 2 | A, T, C |
| d = [A, A] | 0, 1, 2 | T, C, G |
| d = [G, G] | 0, 1, 2 | A, T, C |
| d ∈ Set{CC, GC, TC, AC} | 0, 1, 2 | T, C, G |
| d ∉ Set{AT, CT, TT, CA, AA, CC, GG} | 0, 1, 2 | G, A, T |

(c) starting from the third position in the indexDNA sequence, the conversion is conducted in turn according to the rules shown in the table above by: first, judging which condition in the table the i-th position satisfies, and then performing the corresponding conversion between the ternary number and the base at the i-th position according to the correspondence corresponding with the condition.

Unless otherwise specified, the "indexDNA sequence conversion rule" mentioned in any of the solutions described below refers to the above indexDNA sequence conversion rule.

The present invention also specifically designs a method for preventing mutations that may occur during in vitro manipulation and cell passage, that is, each single-stranded DNA short sequence includes a correctionDNA sequence for checking whether the single-stranded DNA short sequence has a mutation and correcting the mutation.

According to one aspect of the prevent invention, a method for converting data into data DNA sequences is provided, comprising dividing the data into one or more data conversion units, providing a binary number sequence of each data conversion unit, and converting each data conversion unit into a data DNA sequence according to the following steps, thus acquiring a DNA sequence library; the DNA sequence library contains one or more data DNA sequences, and each data DNA sequence is converted from a data conversion unit; the steps comprises: according to the dataDNA sequence conversion rule, converting the binary number sequence of each data conversion unit into a dataDNA sequence, that is, a data DNA sequence;

According to another aspect of the prevent invention, a method for converting data into data DNA sequences is also provided, comprising dividing the data into one or more data conversion units, providing a binary number sequence of each data conversion unit, and converting each data conversion unit into a data DNA sequence according to the following steps, thus acquiring a DNA sequence library; the DNA sequence library contains one or more data DNA sequences, and each data DNA sequence is converted from a data conversion unit; the steps comprises:

(1) converting the position number of the data conversion unit in the data into a ternary number sequence with a fixed number of bits, and then converting the ternary number sequence into an indexDNA sequence according to the indexDNA sequence conversion rule, where the number of bases of the indexDNA sequence is the same as the number of bits of the ternary number sequence;

(2) converting the binary number sequence of the data conversion unit into a dataDNA sequence according to the dataDNA sequence conversion rule;

(3) connecting the indexDNA sequence and the dataDNA sequence of the data conversion unit, and adding a protection sequence of 2 bases in length to the junction to obtain an index+dataDNA sequence, which is a data DNA sequence.

According to another aspect of the present invention, a method for converting data into data DNA sequences including mutation correction sequences is also provided, comprising dividing the data into one or more data conversion units, providing a binary number sequence of each data conversion unit, and converting each data conversion unit into a data DNA sequence including a mutation correction sequence according to the following steps, thus acquiring a DNA sequence library; the DNA sequence library contains one or more data DNA sequences, and each data DNA sequence is converted from a data conversion unit; the steps comprises:

(1) converting the binary number sequence of the data conversion unit into a preliminary data DNA sequence without a mutation correction sequence, the preliminary data DNA sequence including data content information of the data conversion unit;

(2) first, generating a preliminary judgment sequence of 4 bases based on the preliminary data DNA sequence: calculating base number judgment values X(i) when i=A, T, C, G according to the following formula:

$$X(i)=(-1)^{N(i)}$$

wherein i=A, T, C, G; N(i) is the number of base i present in the preliminary data DNA sequence;

storing the base number judgment values X(i) when i=A, T, C, G using the 4 bases of the preliminary judgment sequence respectively, and storing −1 and 1 using C and G respectively, to generate a preliminary judgment sequence;

then, based on the preliminary data DNA sequence, generating a deep judgment sequence of 10 bases: calculating a base bitwise weighted sum of the preliminary data DNA sequence according to the following formula:

$$\text{sum} = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;

converting the value of the base bitwise weighted sum into a 10-bit ternary number sequence to generate a deep judgment sequence;

connecting the preliminary judgment sequence and the deep judgment sequence, and adding a protection base C at the junction to obtain a correctionDNA sequence;

(3) connecting the preliminary data DNA sequence and the correctionDNA sequence, and adding a protection sequence of 2 bases in length at the junction to obtain a data DNA sequence including a mutation correction sequence.

In some preferred embodiments of the method for converting data into data DNA sequences including mutation correction sequences, step (1) comprises: converting the binary number sequence of the data conversion unit into a dataDNA sequence according to the dataDNA sequence conversion rule, the dataDNA sequence being used as a preliminary data DNA sequence without a mutation correction sequence;

In some other preferred embodiments of the method for converting data into data DNA sequences including mutation correction sequences, step (1) comprises:

(1-1) converting the position number of the data conversion unit in the data into a ternary number sequence with a fixed number of bits, and then converting the ternary number sequence into an indexDNA sequence according to the indexDNA sequence conversion rule, wherein the number of bases of the indexDNA sequence is the same as the number of bits of the ternary number sequence;

(1-2) converting the binary number sequence of the data conversion unit into a dataDNA sequence according to the dataDNA sequence conversion rule;

(1-3) connecting the indexDNA sequence with the dataDNA sequence of the data conversion unit, and adding a protection sequence of 2 bases in length at the junction to obtain an index+dataDNA sequence as the preliminary data DNA sequence without a mutation correction sequence.

In this embodiment, each conversion unit of data is converted into a data DNA sequence including position information of the data conversion unit, data content information of the data conversion unit, and a mutation correction sequence, wherein preferably in step (1-3), correctionDNA is connected to one end of the dataDNA in the index+dataDNA sequence.

In other embodiments of the method for converting data into data DNA sequences including mutation correction sequences, other methods can be used in step (1) to convert the binary number sequence of the data conversion unit into a preliminary data DNA sequence without a mutation correction sequence.

The present invention further provides a method for converting encrypted data DNA sequence, comprising:

(1) providing a user name and a password, and randomly generating a corresponding mode between a specific binary number and a specific base in each set of correspondences in the dataDNA sequence conversion rule according to the user name and the password;

(2) converting data into data DNA sequences using any method described above, wherein when the binary number sequence of each data conversion unit is converted into a dataDNA sequence according to the dataDNA sequence conversion rule, the specific binary number is converted into a corresponding specific base according to the corresponding mode generated in step (1).

In some embodiments, any of the data conversion methods described above is implemented on a computer.

According to another aspect of the present invention, a method for storing data using DNA sequences is provided, comprising: converting the data into data DNA sequences using any of the above data conversion methods according to the present invention, synthesizing the DNA sequences, and storing the synthesized DNA sequences.

In an embodiment, the storing of the synthesized DNA sequences is to store the DNA sequences in cells in the form of plasmids, or to integrate the DNA sequences into cell genomes.

According to another aspect of the present invention, a method restoring for restoring DNA sequences obtained by sequencing to data, comprising:

(1) providing DNA sequences obtained by sequencing, wherein the DNA sequences comprise dataDNA sequences representing data content information of data conversion units; and (2) restoring the dataDNA sequences to data according to the dataDNA sequence conversion rule of the present invention.

In some embodiments, step (2) can be restoring the dataDNA sequences to data in binary number form, or step (2) can comprise restoring the dataDNA sequences to data in binary number form and further restoring the data in binary number form to raw data.

The present invention also provides another method for restoring DNA sequences obtained by sequencing to data, comprising:

(1) providing DNA sequences obtained by sequencing, wherein the DNA sequences are a plurality of data DNA sequences, and each data DNA sequence comprises an indexDNA sequence representing the position information of a data conversion unit and a dataDNA sequence representing the data content information of the data conversion unit;

(2) restoring the indexDNA sequence in each data DNA sequence to a ternary number sequence according to the indexDNA sequence conversion rule, and then restoring the ternary number sequence to a position number of the conversion unit in the data;

(3) restoring the dataDNA sequence in each data DNA sequence to data according to the dataDNA sequence conversion rule;

(4) connecting the data restored from the dataDNA sequences of the respective data DNA sequences in the order of their position numbers, to obtain restored data.

In some embodiments, step (3) can be restoring the dataDNA sequence to data in binary number form, or further restoring the data in binary number form to character strings. The restored data obtained in step (4) can be the data in binary number form, or raw data restored from the data in binary number form, or character string data obtained by connecting the character strings obtained in step (3) according to the order of their position numbers, or data further restored from the character string data.

The present invention also provides a method for correcting DNA sequences obtained by sequencing and restoring the same to data, comprising:

(1) providing DNA sequences obtained by sequencing, the DNA sequences comprising preliminary data DNA sequences and mutation correction sequences, wherein the preliminary data DNA sequence comprises data content information of a data conversion unit; the preliminary data DNA sequence in the DNA sequences obtained by sequencing has at most one base mutation;

(2) based on each preliminary data DNA sequence, calculating a base number judgment value X'(i) of the preliminary data DNA sequence according the following formula:

$$X'(i) = (-1)^{N(i)}$$

wherein i=A, T, C, G; N(i) is the number of base i present in the preliminary data DNA sequence;

comparing the base number judgment value X'(i) of the preliminary data DNA sequence with the base number judgment value X(i) obtained by restoration of the preliminary judgment sequence in the mutation correction sequence included in the DNA sequence obtained by sequencing according to the same rule:

if the base number judgment values of two bases change, it indicates that the preliminary data DNA sequence has a base substitution compared to the unmutated preliminary data DNA sequence, and the substitution is a substitution of one of the two bases by the other;

if only the base number judgment value of one base changes, it indicates that the preliminary data DNA sequence has insertion or deletion of this base compared to the unmutated preliminary data DNA sequence;

if none of the base number judgment values of bases changes, it indicates that the preliminary data DNA sequence has no mutation;

(3) based on the preliminary data DNA sequence, calculating a base bitwise weighted sum' of the preliminary data DNA sequence according to the following formula:

$$sum' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;

comparing the base bitwise weighted sum' of the preliminary data DNA sequence with the base bitwise weighted sum obtained by restoration of the deep judgment sequence in the mutation correction sequence included in the DNA sequence obtained by sequencing according to the same rule;

in the case where the preliminary data DNA sequence has a base substitution compared to the unmutated preliminary data DNA sequence: if sum'>sum, the base substitution is that the base having smaller val(i) value is substituted by the base having larger val(i) value; if sum'<sum, the base substitution is that the base having larger val(i) value is substituted by the base having smaller val(i) value; the position coordinate at which the base substitution occurs is the absolute value of the divisor obtained by dividing the difference between sum' and sum by the difference between the val(i) of the two bases; substituting the base at the position by the other of the two bases and correcting the sequence to an unmutated preliminary data DNA sequence;

in the case where the preliminary data DNA sequence has insertion or deletion of one base compared to the unmutated preliminary data DNA sequence;

if sum'>sum, it indicates that base insertion occurs, and the base insertion position is judged as follows: starting from the position where the base appears for the first time in the preliminary data DNA sequence, deleting the base at each position, and calculating a base bitwise weighted sum" of the preliminary data DNA sequence after deletion according to the following formula:

$$sum'' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are deleted;

when the base bitwise weighted sum" calculated after the base at a certain position is deleted is equal to the base bitwise weighted sum obtained by restoration of the deep judgment sequence in the mutation correction sequence included in the DNA sequence obtained by sequencing according to the same rule, the position is the base insertion position; deleting the base at the position and correcting the sequence to an unmutated preliminary data DNA sequence;

if sum'<sum, it indicates that base deletion occurs, and the base deletion position is judged as follows: starting from the first position of the preliminary data DNA sequence, inserting the base to each position, and calculating a base bitwise weighted sum''' of the preliminary data DNA sequence after insertion according to the following formula:

$$sum''' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are inserted;

when the base bitwise weighted sum''' calculated after the base is inserted at a certain position is equal to the base bitwise weighted sum obtained by restoration of the deep judgment sequence in the mutation correction sequence included in the DNA sequence obtained by sequencing according to the same rule, the position is the base deletion position; inserting the base at the position and correcting the sequence to an unmutated preliminary data DNA sequence;

(4) restoring the unmutated preliminary data DNA sequence to data.

In a preferred embodiment of the method for restoring the DNA sequences obtained by sequencing to data, the preliminary data DNA sequence comprises a dataDNA sequence representing data content information of the data conversion unit, and step (4) comprises restoring the dataDNA sequence included in the unmutated preliminary data DNA sequence to data according to the dataDNA sequence conversion rule. In some embodiments, step (4) can be restoring the dataDNA sequence included in the unmutated preliminary data DNA sequence to data in binary number form, or further restoring the data in binary number form to raw data.

In other preferred embodiments of the method for restoring the DNA sequences obtained by sequencing to data, in the method, the DNA sequences obtained by sequencing are a plurality of data DNA sequences, and the preliminary data DNA sequence of each data DNA sequence comprises an indexDNA sequence representing the position information of the data conversion unit and a dataDNA sequence representing the data content information of the data conversion unit, and step (4) comprises:

(4-1) restoring the indexDNA sequence in each data DNA sequence to a ternary number sequence according to the indexDNA sequence conversion rule, and then restoring the ternary number sequence to a position number of the conversion unit in the data;

(4-2) restoring the dataDNA sequence in each data DNA sequence to data according to the dataDNA sequence conversion rule;

(4-3) connecting the data restored from the dataDNA sequences of the respective data DNA sequences in the order of their position numbers, to obtain restored data.

Step (4-2) can be restoring the dataDNA sequence to data in binary number form, or further comprise restoring the data in binary number form to character strings; and the restored data in step (4-3) is data in binary number form, or the raw data obtained by further restoring the data in binary number form, or character string data obtained by connecting the character strings restored from the dataDNA sequence according to the order of their position numbers, or data further restored from the character string data.

The present invention also provides a method for restoring encrypted DNA sequences obtained by sequencing to data, comprising:

(1) providing a user name and a password to obtain a corresponding mode between a specific binary number and a specific base in each set of correspondences in the dataDNA sequence conversion rule; wherein the corresponding mode is the one set for the same user name and password when data is converted into encrypted DNA sequences;

(2) restoring the encrypted DNA sequences obtained by sequencing to data using any data restoration method described above to data, wherein when the dataDNA sequence of each DNA sequence is restored to data according to the dataDNA sequence conversion rule, the specific base is restored to a corresponding specific binary number according to the corresponding mode generated in step (1).

In some embodiments, any of the data conversion methods according to the present invention is implemented on a computer.

According to another aspect of the prevent invention, a method for acquiring data from cells is provided, comprising: extracting DNA sequences storing data information from cells, sequencing, and restoring the DNA sequences obtained by sequencing to raw data by any of the data restoring methods according to the present invention.

According to another aspect of the prevent invention, a system for converting data into data DNA sequences is provided, comprising an input unit and a dataDNA sequence conversion unit; wherein the input unit is configured to provide binary number sequences of data conversion units;

wherein the dataDNA sequence conversion unit is configured to convert the binary number sequences of the data conversion units into dataDNA sequences according to the dataDNA sequence conversion rule.

In some embodiments, the system for converting data into data DNA sequences further comprises an indexDNA generation unit and a first integration unit; wherein, the indexDNA sequence generation unit is configured to convert the position number of the data conversion unit in the data into a ternary number sequence with a fixed number of bits, and then convert the ternary number sequence into an indexDNA sequence according to the indexDNA sequence conversion rule, wherein the number of bases of the indexDNA sequence are the same as the number of bits of the ternary number sequence; wherein, the first integration unit is configured to connect the indexDNA sequence and the dataDNA sequence of the data conversion unit, and add a protection sequence of 2 bases in length at the junction to obtain an index+dataDNA sequence.

The present invention also provides a system for converting data into data DNA sequences with mutation correction sequences, comprising an input unit, a preliminary data DNA conversion unit, a correctionDNA sequence generation unit, and a second integration unit;

wherein the input unit is configured to provide binary number sequences of data conversion units;

wherein the preliminary data DNA conversion unit is configured to convert the binary number sequence of each data conversion unit into a preliminary data DNA sequence without a mutation correction sequence, the preliminary data DNA sequence including data content information of the data conversion unit;

wherein the correctionDNA sequence generation unit is configured to generate a correctionDNA sequence by the following method:

first, a preliminary judgment sequence of 4 bases is generated based on the preliminary data DNA sequence: base number judgment values X(i) when i=A, T, C, G are calculated according to the following formula:

$$X(i)=(-1)^{N(i)}$$

wherein i=A, T, C, G; N(i) is the number of base i present in the preliminary data DNA sequence;

the base number judgment values X(i) when i=A, T, C, and G are stored using the 4 bases in the preliminary judgment sequence respectively, and −1 and 1 are stored using bases C and G respectively, to generate a preliminary judgment sequence;

then, based on the preliminary data DNA sequence, a deep judgment sequence of 10 bases is generated: a base bitwise weighted sum of the preliminary data DNA sequence is calculated according to the following formula:

$$\text{sum} = \sum_{i=1}^{N} val(i) * \text{position}(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;

the value of the base bitwise weighted sum is converted into a 10-bit ternary number sequence to generate a deep judgment sequence;

the preliminary judgment sequence and the deep judgment sequence are connected, and a protection base C is added at the junction to obtain a correctionDNA sequence;

wherein, the second integration unit is configured to connect the preliminary data DNA sequence and the correctionDNA sequence, and add a protection sequence of 2 bases in length at the junction to obtain a data DNA sequence including a mutation correction sequence.

In some preferred embodiments, the preliminary data DNA sequence conversion unit is a dataDNA sequence conversion unit which is configured to convert the binary number sequence of the data conversion unit into a dataDNA sequence according to the dataDNA sequence conversion rule, and the dataDNA sequence is used as the preliminary data DNA sequence without a mutation correction sequence;

In some other preferred embodiments, the preliminary data DNA sequence conversion unit comprises an indexDNA sequence generation unit, a dataDNA sequence conversion unit and a third integration unit; wherein, the indexDNA sequence generation unit is configured to convert the position number of the data conversion unit in the data into a ternary number sequence with a fixed number of bits, and then convert the ternary number sequence into an indexDNA sequence according to the indexDNA sequence conversion rule, wherein the number of bases of the indexDNA sequence is the same as the number of bits of the ternary number sequence; wherein, the dataDNA sequence conversion unit is configured to convert the binary number sequence of the data conversion unit into a dataDNA sequence; wherein, the third integration unit is configured to connect the indexDNA sequence with the dataDNA sequence of the data conversion unit, and add a protection sequence of 2 bases in length at the junction to obtain an index+dataDNA sequence as the preliminary data DNA sequence without a mutation correction sequence. Preferably, the second integration unit is configured to connect the correctionDNA sequence to one end of the dataDNA sequence in the preliminary data DNA sequence, and add a protection sequence of 2 bases in length at the junction to obtain a data DNA sequence including a mutation correction sequence;

Any of the aforementioned data conversion systems may further comprise an encryption unit comprising a user name and password input unit and a dataDNA sequence conversion rule random generation unit; wherein the user name and password input unit is configured to provide a user name and a password; wherein the dataDNA sequence conversion rule random generation unit is configured to randomly generate a corresponding mode between a specific binary number and a specific base in each set of correspondences in the dataDNA sequence conversion rule according to the user name and the password; wherein the dataDNA sequence conversion unit is configured to convert the binary number sequence of the data conversion unit into an encrypted dataDNA sequence according to the dataDNA sequence conversion rule, wherein the specific base is converted into a corresponding specific binary number according to the corresponding mode randomly generated by the dataDNA sequence conversion rule random generation unit.

According to another aspect of the present invention, a system for restoring DNA sequences obtained by sequencing to data is provided, comprising an input unit and a dataDNA sequence restoration unit; wherein the input unit is configured to provide DNA sequences obtained by sequencing, each DNA sequence comprising a dataDNA sequence representing data content information of a data conversion unit; wherein the dataDNA sequence restoration unit is configured to restore the dataDNA sequences to data according to the dataDNA sequence conversion rule.

In some embodiments, the dataDNA sequence restoration unit is configured to restore the dataDNA sequences to data in binary number form, or to restore the dataDNA sequence to data in binary number form and further restore the data in binary number form to raw data.

The present invention also provides another system for restoring DNA sequences obtained by sequencing to data, comprising an input unit, an indexDNA sequence restoration unit and a fourth integration unit; wherein the input unit is configured to provide DNA sequences obtained by sequencing, the DNA sequences obtained by sequencing being a plurality of data DNA sequences, and each data DNA sequence comprising an indexDNA sequence representing the position information of the data conversion unit and a dataDNA sequence representing the data content information of the data conversion unit; wherein the indexDNA sequence restoration unit is configured to restore the indexDNA sequence in each data DNA sequence to a ternary number sequence according to the indexDNA sequence conversion rule, and then restore the ternary number sequence to a position number of the conversion unit in the data; wherein the dataDNA sequence restoration unit is configured to restore the dataDNA sequence in each data DNA sequence to data according to the dataDNA sequence conversion rule; wherein the fourth integration unit is configured to connect the data restored from the dataDNA sequences of the respective data DNA sequences in the order of their position numbers, to obtain restored data.

In some embodiments, the dataDNA sequence restoration unit is configured to restore the dataDNA sequence to data in binary number form, or to restore the dataDNA sequence to data in binary number form and further restore the data in binary number form to character strings; the fourth integration unit is configured to obtain the restored data in binary number form, or obtain raw data further restored from the data in binary number form, or to connect the character strings restored by the dataDNA sequence restoration unit according to the order of their position numbers to obtain character string data, or obtain raw data further restored from the character string data.

The present invention also provides a system for correcting DNA sequences obtained by sequencing and restoring the same to data, comprising an input unit, a correction unit and a preliminary data DNA sequence restoration unit;

wherein the input unit is configured to provide DNA sequences obtained by sequencing, the DNA sequences comprising preliminary data DNA sequences and mutation correction sequences, wherein each preliminary data DNA sequence comprises data content information of a data conversion unit; the preliminary data DNA sequence in the DNA sequences obtained by sequencing has at most one base mutation;

wherein the correction unit is configured to restore the preliminary data DNA sequences to unmutated preliminary data DNA sequences by the following method:

(a) based on each preliminary data DNA sequence, calculating a base number judgment value X'(i) of the preliminary data DNA sequence according the following formula:

$$X'(i) = (-1)^{N(i)}$$

wherein i=A, T, C, G; N(i) is the number of base i present in the preliminary data DNA sequence;

comparing the base number judgment value X'(i) of the preliminary data DNA sequence with the base number judgment value X(i) obtained by restoration of the preliminary judgment sequence in the mutation correction sequence included in the DNA sequence obtained by sequencing according to the same rule:

if the base number judgment values of two bases change, it indicates that the preliminary data DNA sequence has a base substitution compared to the unmutated preliminary data DNA sequence, and the substitution is a substitution of one of the two bases by the other;

if only the base number judgment value of one base changes, it indicates that the preliminary data DNA sequence has insertion or deletion of this base compared to the unmutated preliminary data DNA sequence;

if neither of the base number judgment values of bases changes, it indicates that the preliminary data DNA sequence has no mutation;

(b) based on the preliminary data DNA sequence, calculating a base bitwise weighted sum' of the preliminary data DNA sequence according to the following formula:

$$sum' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;

comparing the base bitwise weighted sum' of the preliminary data DNA sequence with the base bitwise weighted sum obtained by restoration of the deep judgment sequence in the mutation correction sequence included in the DNA sequence obtained by sequencing according to the same rule:

in the case where the preliminary data DNA sequence has a substitution of two bases compared to the unmutated preliminary data DNA sequence: if sum'>sum, the base substitution is that the base having smaller val(i) value is substituted by the base having larger val(i) value; if sum'<sum, the base substitution is that the base having larger val(i) value is substituted by the base having smaller val(i) value; the position coordinate at which the base substitution occurs is the absolute value of the divisor obtained by dividing the difference between sum' and sum by the difference between the val(i) of the two bases; substituting the base at the position by the other of the two bases and correcting the sequence to an unmutated preliminary data DNA sequence;

in the case where the preliminary data DNA sequence has insertion or deletion of one base compared to the unmutated preliminary data DNA sequence;

if sum'>sum, it indicates that base insertion occurs, and the base insertion position is judged as follows: starting from the position where the base appears for the first time in the preliminary data DNA sequence, deleting the base at each position, and calculating a base bitwise weighted sum" of the preliminary data DNA sequence after deletion according to the following formula:

$$sum'' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are deleted;

when the base bitwise weighted sum" calculated after the base at a certain position is deleted is equal to the base bitwise weighted sum obtained by restoration of the deep judgment sequence in the mutation correction sequence included in the DNA sequence obtained by sequencing according to the same rule, the position is the base insertion position; deleting the base at the position and correcting the sequence to an unmutated preliminary data DNA sequence;

if sum'<sum, it indicates that base deletion occurs, and the base deletion position is judged as follows: starting from the first position of the preliminary data DNA sequence, inserting the base to each position, and calculating a base bitwise weighted sum''' of the preliminary data DNA sequence after insertion according to the following formula:

$$sum''' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are inserted;

when the base bitwise weighted sum''' calculated after the base is inserted at a certain position is equal to the base bitwise weighted sum obtained by restoration of the deep judgment sequence in the mutation correction sequence contained in the DNA sequence obtained by sequencing according to the same rule, the position is the base deletion position; inserting the base at the position and correcting the sequence to an unmutated preliminary data DNA sequence;

wherein the preliminary data DNA sequence restoration unit is configured to restore the unmutated preliminary data DNA sequence to data.

In some preferred embodiments of the system for correcting DNA sequences obtained by sequencing and restoring the same to data, the preliminary data DNA sequence comprises a dataDNA sequence representing data content information of the data conversion unit, and the preliminary data DNA sequence restoration unit is a dataDNA sequence restoration unit, configured to restore the dataDNA sequence included in the unmutated preliminary data DNA sequence to data according to the dataDNA sequence conversion rule. In a further embodiment, the dataDNA sequence restoration unit is configured to restore the dataDNA sequence included in the unmutated preliminary data DNA sequence to data in binary number form, or restore the dataDNA sequence included in the unmutated preliminary data DNA sequence to data in binary number form and further restore the data in binary number form to raw data.

In some other preferred embodiments of the system for correcting DNA sequences obtained by sequencing and restoring the same to data, the DNA sequences obtained by sequencing are a plurality of data DNA sequences, and the preliminary data DNA sequence of each data DNA sequence comprises an indexDNA sequence representing the position information of the data conversion unit and a dataDNA sequence representing the data content information of the data conversion unit, and the preliminary data DNA sequence restoration unit comprises an indexDNA restoration unit, a dataDNA sequence restoration unit and a fifth integration unit;

wherein the indexDNA sequence restoration unit is configured to restore the indexDNA sequence in each data DNA sequence to a ternary number sequence according to the indexDNA sequence conversion rule, and then restore the ternary number sequence to a position number of the conversion unit in the data;

wherein the dataDNA sequence restoration unit is configured to restore the dataDNA sequence in each data DNA sequence to data according to the dataDNA sequence conversion rule;

wherein the fifth integration unit is configured to connect the data restored from the dataDNA sequences of the respective data DNA sequences in the order of their position numbers, to obtain the restored data;

wherein the dataDNA sequence restoration unit is configured to restore the dataDNA sequence to data in binary number form, or to further restore the data in binary number form to character strings; the fifth integration unit is configured to obtain the restored data in binary number form, or to further obtain raw data from the data in binary number form, or to connect the character strings restored by the dataDNA sequence restoration unit according to the order of their position numbers to obtain character string data, or to obtain data further restored from the character string data.

Any of the aforementioned data restoration systems of the present invention can further comprise a decryption device, the encryption unit comprising an input unit and a dataDNA sequence conversion rule determination unit;

wherein the input unit is configured to provide a user name and a password;

wherein the dataDNA sequence conversion rule determination unit is configured to obtain a corresponding mode between a specific binary number and a specific base in each set of correspondences in the dataDNA sequence conversion rule according to the user name and the password, the corresponding mode being the one set for the same user name and password when the data is converted into the encrypted DNA sequence.

In the system comprising a decryption device, the dataDNA sequence restoration unit is configured to convert the dataDNA sequences in the encrypted DNA sequences obtained by sequencing to data according to the dataDNA sequence conversion rule, wherein the specific base is restored to the corresponding specific binary number according to the corresponding mode determined by the dataDNA sequence conversion rule determination unit.

According to another aspect of the invention, an executable software product comprising program instructions stored on a computer readable storage medium is provided, wherein the software product can be executed by a computer to convert data into data DNA sequences, and the software product comprises program instructions for executing any of the data conversion methods described in the invention.

According to another aspect of the invention, an executable software product comprising program instructions stored on a computer readable storage medium is provided, wherein the software product can be executed by a computer to restore the DNA sequences obtained by sequencing to data, and the software product comprises program instructions for executing any of the data restoration methods according to the present invention.

According to another aspect of the invention, a computer readable storage medium storing any of the software products of the present invention is provided.

The methods and devices according to the present invention can prevent the generation of an initiation codon in the data DNA sequences, prevent the generation of a continuously repeated single-base sequence in the data DNA sequences, and handle data DNA mutations that may occur. By separately designing the dataDNA module, the indexDNA module and the correctionDNA module, the present invention finally integrates the data DNA sequences, restores the DNA sequences to the raw data, and stores a large amount of data in the biological organisms.

BRIEF DESCRIPTION OF THE DRAWINGS

FIG. 11 shows a data DNA sequence library obtained by converting the emblem and song lyrics of Tsinghua University using the method of the present invention, scrambling sequence positions and introducing single base mutations.

DETAILED DESCRIPTION OF THE PREFERRED EMBODIMENTS

Figure 1:
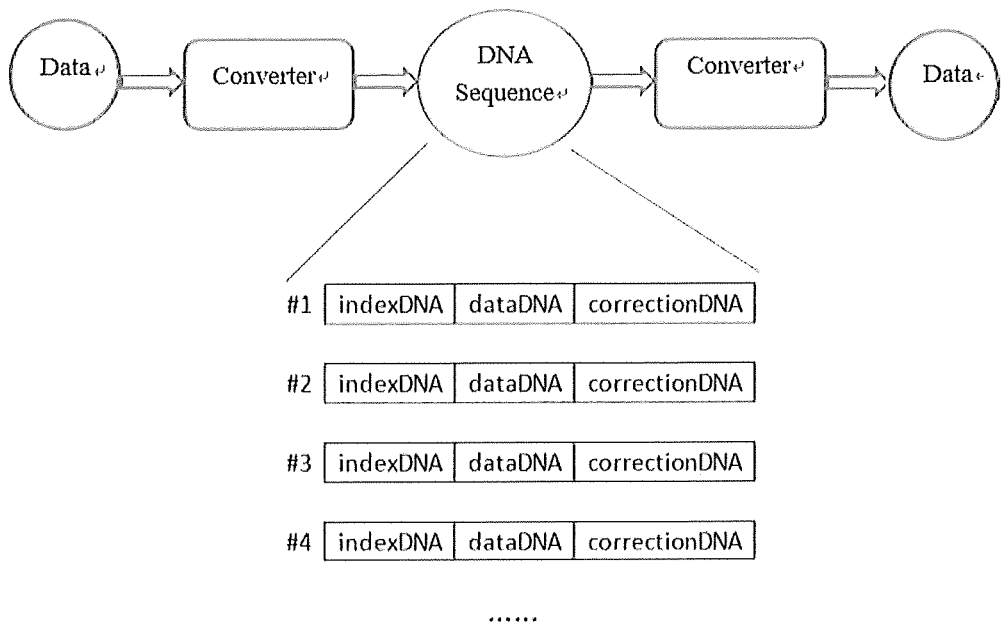
FIG. 1 is a schematic diagram of an example of data conversion and data restoration according to the present invention.

In the present invention, the term "data" indicates any form of carrier capable of expressing information. "Data" includes, but is not limited to, symbols, characters, numbers, voices, images, videos, and the like. The data can be in binary number form, hexadecimal form or character string form, or any other forms that can be converted directly or indirectly into binary number form.

In the present invention, the terms "base" and "nucleotide" are used interchangeably and refer to A, T, C or G constituting a DNA sequence.

The term "data DNA sequence" used in the present invention refers to a DNA sequence converted from data, and is a DNA sequence in the form of data. During storage, the compound DNA sequence is synthesized according to the data DNA sequence and stored in the cell.

The term "data conversion unit" and "conversion unit" used in the present invention are interchangeable, referring to a component of data. When data is converted into data DNA sequences, conversion is performed in units of data conversion units, and one data conversion unit is converted to one data DNA sequence. When the amount of data is small, all data consists of one data conversion unit, which is converted into a data DNA sequence for storage. When the amount of data is large, since the DNA sequence converted from the complete data is long and inconvenient to synthesize and store in cells, the data is divided into a plurality of conversion units, and the binary number sequence corresponding to each conversion unit has a specific length. Each conversion unit is converted into a data DNA sequence, and the entire data is converted into a plurality of data DNA sequences, so that each DNA sequence can be separately synthesized and stored in the cell. When the data is divided into a plurality of conversion units, the binary number sequence corresponding to the data content information of each conversion unit preferably has the same length. The plurality of data DNA sequences constitutes a data DNA library. A set comprising the plurality of data DNA sequences, such as cells for storing the plurality of data DNA sequences, may also be referred to as a data DNA library.

When the amount of data is small, all data can form one data conversion unit, that is, all data is divided into one data conversion unit. At this point, for example, the data is first converted into binary numbers in bytes, and then all the bytes are connected in sequence to form a binary number sequence of data. In some cases, in each 8-bit byte in the binary numbers converted from raw data, the data information may occupy only 7 bits. For example, if the raw data is character strings or can be converted into character strings, the data information can be stored only by the 7-bit binary number sequences, and all the 7-bit binary number sequences indicating the data content information are connected in sequence to form the binary number sequence of the data conversion unit.

When the amount of data is large, the data is divided into a plurality of conversion units. The binary number sequence corresponding to the data content information of each conversion unit has a specific length. The "specific length" may be 70-240 bits, preferably 140-175 bits. The raw data can be first converted into binary number sequences, and then divided into a plurality of conversion units, or first divided into a plurality of character string units, and then each character string unit is converted into a binary number sequence. In an example, the raw data can be first converted into binary numbers in bytes, and then a specific number of bytes are connected in sequence to form a binary number sequence of the conversion unit. One byte refers to an 8-bit binary number sequence, as is well known to those skilled in the art. In some cases, in each 8-bit byte in the binary numbers converted from raw data, the data information may occupy only 7 bits. For example, if the raw data is character strings or can be converted into character strings, the data information can be stored only by the 7-bit binary number sequences, and the specific number of 7-bit binary number sequences is connected in sequence to form a conversion unit. In another example, in the case where the raw data is character strings or can be converted into character strings, the raw data can be first divided into character string units of a specific length, then each character in the character string is converted into a binary number sequence, and the binary number sequence corresponding to each character in the character string unit is sequentially connected to form a binary number sequence of the conversion unit.

In the present invention, the indexDNA sequence includes position information of each data conversion unit in the data. When data is converted, the position number of each data conversion unit in the data is first converted into a ternary number sequence, and then the ternary number sequence is converted into an indexDNA sequence. The number of bits of the ternary number sequence converted from the position number of the conversion unit in the data, or the number of bases of the indexDNA sequence may be 5-15, preferably 11-15, and most preferably the maximum number is 15. The number of bases of the indexDNA sequence determines the size of a library constructed. When the number of indexDNA bases is 15 nt, a data DNA library can contain up to ($3^{15}$-1=14,348,906) data DNA sequences. Since each data DNA sequence stores a data text of 20 characters, each data DNA library can store up to about 300 MB of data. When the amount of data to be converted is smaller or larger, the length of indexDNA sequence can also be reduced or increased as needed. Reducing the length of the indexDNA sequence can improve the conversion efficiency, and increasing the length of the indexDNA sequence can increase the amount of information stored in the DNA sequence.

The "protection sequence" described in the present invention is a sequence added at the junction of an indexDNA sequence and a dataDNA sequence, or at the junction of a dataDNA sequence and a correctionDNA sequence. The protection sequence should be able to ensure that no sequence combination in S={ATG CTG TTG CAT, CAG CAA, AAA, TTT, CCC, GGG} is formed at the junction of the indexDNA sequence and the dataDNA sequence as well as at the junction of the dataDNA sequence and the correctionDNA sequence. In the present invention, the protection sequence is preferably CG.

In the present invention, the order of connection of the indexDNA sequence and the dataDNA sequence in the index+dataDNA sequence is not limited, that is, the indexDNA sequence at the 5' end, and the dataDNA sequence at the 3' end, or the dataDNA sequence at the 5' end, and the indexDNA sequence at the 3' end.

In the present invention, the order of connection of the preliminary judgment sequence and the deep judgment sequence in the correctionDNA sequence is not limited, that is, the preliminary judgment sequence at the 5' end, and the deep judgment sequence at the 3' end, or the deep judgment sequence at the 5' end, and the judgment sequence at the 3' end.

In the present invention, when a plurality of members in one set respectively correspond to a plurality of members in another set (for example, some numbers respectively correspond to certain bases, or some variables respectively correspond to certain values), or a plurality of members in a set respectively store a plurality of members in another set (for example, some bases respectively store certain numbers), unless otherwise specified, it is not limited for each member in a set to correspond to a specific member in another set, and each member in a set can correspond to any member in another set. However, those skilled in the art should appreciate that in the steps that are continuously performed, mutually compared, or have a responding relationship, if it is necessary to apply a correspondence between a certain set and its corresponding set, the correspondence between the specific members in the set and the specific members in its corresponding set should be consistent.

Specifically, for example, according to the present invention, in the indexDNA sequence conversion rule and the dataDNA conversion rule, in the correspondence between each set of ternary numbers or binary numbers and bases, different bases respectively correspond to different ternary numbers or binary numbers, for the purpose of storing data information. The specific base corresponding to each number in each set of ternary numbers or binary numbers is not limited, and each number in each set of ternary numbers or binary numbers can correspond to any of bases in the corresponding set. In an example, when a set of ternary numbers 0, 1, 2 corresponds to a set of bases A, T, C, it can be 0=A, 1=T, 2=C, or 0=T, 1=C, 2=A, or 0=T, 1=A, 2=C, or other corresponding mode. However, when a conversion rule is applied to different conversion units in the same set of data, the corresponding modes between specific ternary numbers or binary numbers and specific bases should be the same under the same condition. The "same condition" means that the conditions in the conversion rule table (including an indexDNA sequence conversion rule table and a dataDNA conversion rule table) belong to the same set. Each row in the conversion rule table is a set.

In another example, when the data DNA sequence obtained by sequencing is restored to raw data, the corresponding mode between certain numbers and certain bases, as well as certain variables and certain values involved therein should be the same as that between the numbers and bases as well as the variables and values used in generation of the data DNA sequence.

In another example, according to the method for restoring data DNA sequences obtained by sequencing to raw data, when the base bitwise weighted sums of different sequences are compared to determine which type of mutation occurs, the ways to take value of val(i) in the calculation formula of the compared base bitwise weighted sums should be the same.

Those skilled in the art will appreciate that, in the present invention, when the data DNA sequence obtained by sequencing is restored to raw data, the indexDNA sequence conversion rule as the basis for converting an indexDNA sequence into a ternary number sequence is the same as the indexDNA sequence conversion rule used in generation of the indexDNA sequence, and the dataDNA sequence conversion rule as the basis for converting a raw dataDNA sequence into a binary number sequence is the same as the dataDNA sequence conversion rule used in generation of the raw dataDNA sequence. "The same indexDNA sequence conversion rule" or "the same dataDNA sequence conversion rule" described herein indicates the same corresponding mode between a specific binary number and a specific base in each set of correspondences in these conversion rules.

The "corresponding mode between a specific binary number and a specific base in each set of correspondences" according to the present invention means the corresponding mode in which each specific binary number corresponds to a specific base.

In the process of encryption and decryption according to the method of the present invention, different corresponding modes between a specific binary number and a specific base in each set of correspondences in the dataDNA sequence conversion rules are set for different user names (referred to as corresponding mode in this paragraph). In the encrypted data conversion method, a corresponding mode is randomly generated according to the input user name, and in the decryption process of the data restoration method, the corresponding mode generated for the user name is obtained according to the input user name, and then data is restored according to the corresponding mode.

In the present invention, when mutation test and correction are performed on a DNA sequence, a base number judgment value and a base bitwise weighted sum of the sequence need to be calculated and compared with those in the correctionDNA sequence included in the DNA sequence. The base number judgment value and the base bitwise weighted sum of the sequence represent corresponding values of an unmutated sequence. By comparison, whether the DNA sequence has been mutated relative to the unmutated sequence can be clear. Those skilled in the art should appreciate that, when comparing again, the calculation formula and corresponding mode used to calculate the base number judgment value and the base bitwise weighted sum of the DNA sequence should be the same as those used to obtain the base number judgment value and the base bitwise weighted sum in the correctionDNA sequence included in the DNA sequence. The term "corresponding mode" as described herein means: (1) a specific corresponding mode for the base number judgment value, C/G and −1/1; and/or (2) a specific corresponding mode for the base bitwise weighted sum, val(A), val(T), val(C), val(G), and 1, 2, 3, 4.

In the present invention, the "position number" is preferably a decimal number, but may be any number that can indicate the position order and can be converted to and from a ternary number.

In the present invention, "mutation of one base" refers to that one base is substituted by the other base, or one base is inserted or deleted.

In the present invention, the term "data conversion method" refers to a method for converting data into data DNA sequences, a method for converting data into data DNA sequences comprising mutation correction sequences, a method for converting data into encrypted data DNA sequences or an encrypted data conversion method. The term "data restoration method" refers to a method for restoring DNA sequences obtained by sequencing to data or a method for restoring encrypted DNA sequences obtained by sequencing to data.

The DNA sequences obtained using the data conversion method of the present invention are suitable for being stored in cells. The cells for storing the DNA sequence in the present invention can be microbial cells, such as bacteria, *E. coli* cells or fungal cells, *Saccharomyces cerevisiae* or any other suitable cells or cell lines, such as insect cells or mammalian cells or cell lines. The DNA sequences obtained using the data conversion method of the present invention can be stored in cells in the form of plasmids, or integrated into cell genomes.

The DNA sequences obtained by the data conversion method of the present invention can be introduced into a cell for storage by any appropriate means, for example, the DNA sequences are cloned into a eukaryotic expression vector, and then directly converted into a yeast cell for passage storage, or the DNA sequences are directly integrated into a yeast genome for storage. The DNA sequences stored in a cell can be extracted by any appropriate means, for example, directly extracting plasmids from yeast, converting the same into *E. coli* for amplification, and extracting the plasmids again for sequencing, or directly extracting the yeast genome for PCR amplification, and taking the target fragment for sequencing.

As an example of storing the DNA sequences obtained by the data conversion method of the present invention in cells in the form of plasmids, it can be operated according to the following steps: synthesizing a plurality of single-stranded DNA sequences based on the data DNA sequence library converted from data, each single-stranded DNA sequence having restriction enzyme cutting sites corresponding to the plasmid at both ends; then performing enzyme cutting and connection on each single-stranded DNA sequence and plasmid, inserting a single-stranded DNA sequence into each plasmid, converting the connected plasmids into *E. coli* for amplification, extracting the amplified plasmids and performing restriction enzyme cutting detection, and converting the plasmids without error into yeast cells. The yeast cells are then subcultured. The plasmids containing respective single-stranded DNA sequences can be mixed and then converted into the yeast cells.

As an example of integrating the DNA sequences obtained by the data conversion method of the present invention into cell genomes, it can be operated according to the following steps: synthesizing a plurality of single-stranded DNA sequences based on the data DNA sequence library converted from data, each single-stranded DNA sequence having restriction enzyme cutting sites corresponding to the plasmid at both ends; then performing enzyme cutting and connection on each single-stranded DNA sequence and plasmid, inserting a single-stranded DNA sequence into each plasmid, converting the connected plasmids into *E. coli* for amplification, extracting the amplified plasmids and performing restriction enzyme cutting detection, performing restriction enzyme on the plasmids without error to obtain target fragments (i.e., the single-stranded DNA sequences), then connecting homologous sequences to both ends, and performing homologous recombination on the target fragments having the homologous sequences connected to both ends and the yeast cells to integrate the target fragments into the genomes of the yeast cells. The yeast cells are then subcultured. The fragments containing respective single-stranded DNA sequences can be homologously recombined with the yeast cells.

Those skilled in the art could recognize that the above steps are merely illustrative and that DNA sequences can be introduced into cells by other methods. The cells used to store DNA sequences are also not limited to yeast cells. Appropriate methods for introducing DNA sequences into cells and appropriate cells for storing DNA sequences are well known to those skilled in the art.

"One or more" as used in the present invention means one, two or more than two. "One or more strands" as used in the present invention means one, two or more than two strands.

It shall be appreciated that the following description is merely an illustration rather than a limitation to the scope of the invention, and that the scope of the invention is determined by the claims. The present invention may be implemented in other specific methods without departing from the scope and spirit of the invention. Various modifications and improvements may be made to the following embodiments by those skilled in the art, such as changing the specific parameters used in the present invention, without departing from the scope and spirit of the invention.

FIG. 1 is a schematic diagram of an example of data conversion and data restoration according to the present invention. Data is converted to a set of a series of single-stranded DNA short sequences (i.e., data DNA sequences) by the designed conversion algorithm, and the set of single-stranded DNA short sequences can be restored to raw data by the restoration algorithm. Each single-stranded DNA short sequence consists mainly of three parts: indexDNA, including position information of the DNA sequence in the entire DNA sequences set, that is, position information of data content in the entire data; dataDNA, including data content information; and correctionDNA for checking mutations in the DNA sequence. A protection sequence CG of 2 bases in length is provided between the indexDNA sequence and the dataDNA sequence, and between the dataDNA sequence and the correctionDNA sequence, respectively.

Example 1. Conversion and Restoration of Text Data

The data conversion process and restoration process of the present invention will be described below by taking the data of text type as an example.

Figure 2:
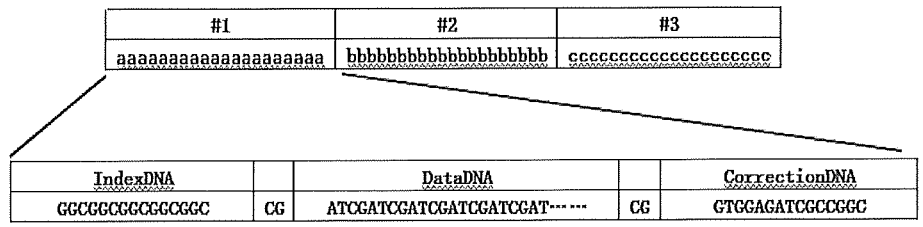
FIG. 2 is a schematic diagram of text data conversion.

Different types of data have been pre-processed, and the data format has been converted to a text file "written" by characters in the ASCII table. Therefore, the converter will face a string of text, which can also be interpreted as a long sequence of strings. The data text is to be converted to data DNA sequences based on character string units of the data text. As shown in FIG. 2, every 20 characters form a string, which is a conversion unit and is encoded into a single-stranded data DNA sequence. Starting from the first conversion unit (#1) of the data text, all conversion units (#2, #3, etc.) are sequentially encoded to generate a plurality of single-stranded data DNA sequences.

Generation and Restoration of indexDNA Sequence
(1) Generation Algorithm for indexDNA Sequence The information stored in an indexDNA sequence is a decimal number indicating the character string unit of the data text corresponding to the single-stranded data DNA sequence. When the length of the indexDNA sequence is 15 nt, a data DNA library can include up to ($3^{15}$-1=14,348,906) data DNA sequences. Each data DNA sequence stores a data text of 20 characters, so each data DNA library can store up to about 300 MB of data.

Figure 3:
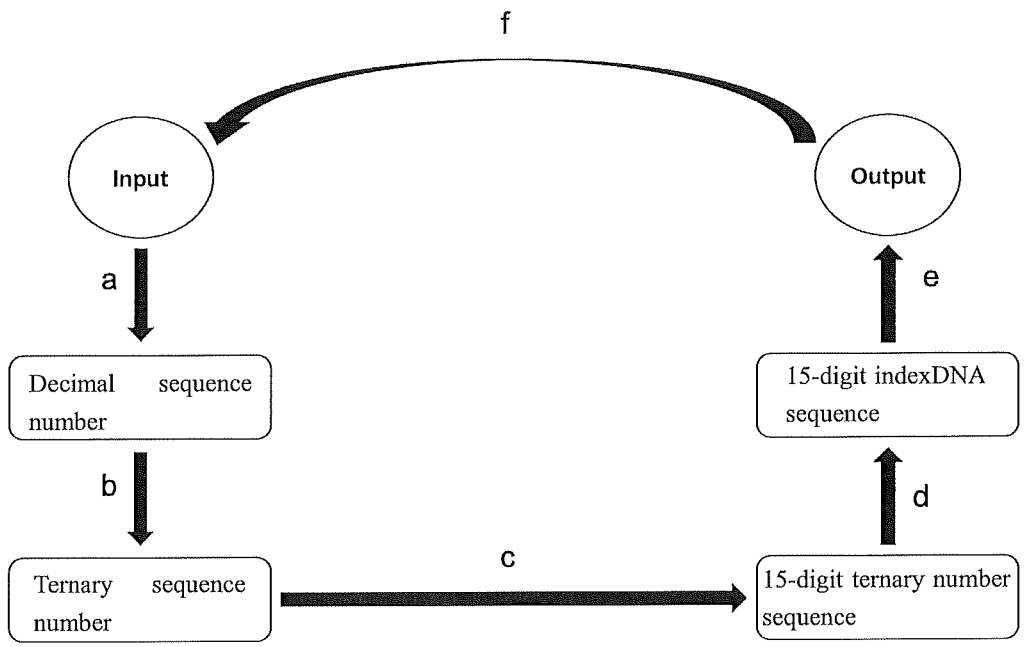
FIG. 3 shows a generating process of an indexDNA sequence.

FIG. 3 shows the process of generating an indexDNA sequence. When encoding proceeds to the Nth conversion unit of the data text, an indexDNA generation module accepts the decimal sequence number N as the start data of encoding (as shown in the process a in FIG. 3); then the decimal number N is converted into a ternary number by an algorithm of converting decimal numbers into ternary numbers (as shown in the process b in FIG. 3, the core of the algorithm of converting decimal numbers into ternary numbers is to divide N by 3 and take the remainder, then divide the resulting quotient by 3 and take the remainder, and so on until the quotient is less than 3); after the ternary number is obtained, it is converted into a 15-digit ternary number sequence of which the initial state is set to "000000000000000", and the insufficient digits are complemented by "0" (as shown in the process c in FIG. 3); after that, the 15-digit ternary number sequence is encoded using a conversion algorithm into an indexDNA sequence of 15 nt in length, and meanwhile, the 15-digit ternary number sequence returns to the initial state and waits for the next cycle (as shown in the process d in FIG. 3); finally, the indexDNA sequence is output, and integrated with its corresponding dataDNA sequence before proceeding to next operation, and the indexDNA generation module will encode next character string unit. When N=N+1, the process described above is continued (as shown in the process e/f in FIG. 3).

The process d in FIG. 3, that is, the process of encoding the 15-digit ternary number sequence into a 15-digit indexDNA sequence, is the key to realize the function of this part, and its algorithm design is shown in Table 1.

An initiation codon sequence and single-base repetitive sequences should be avoided in the indexDNA sequence. That is, it is necessary to prevent the occurrence of sequence combinations in set S={ATG CTG TTG CAT, CAG CAA, AAA, TTT, CCC, GGG}. In order to achieve this, when the i-th position of the indexDNA sequence is encoded, the base types on the i−2th and i−1th positions that have been encoded are first judged, and then which type of base is encoded at this position is determined. That is, the encoding of the base at the i-th position is simultaneously restricted by the information of the two base sequences ahead and the type of the ternary number that needs to be stored at the site.

TABLE 1 indexDNA sequence onversion algorithm

| Column No. | 0 | 1 | 2 | 3 | 4 | 5 | 6 | 7 |
|---|---|---|---|---|---|---|---|---|
| d | AT | CT | TT | CA | AA | GG | CC, GC, TC, AC | $X^2$/D |
| Number of Sd elements | 3 | 3 | 2 | 1 | 3 | 3 | 3 | 4 |
| Sd | A | A | A |   |   | A |   | A |
|  | T | T | T |   | T | T | T | T |
|  | C | C | C | C | C | C | C | C |
|  |   |   |   |   | G |   | G | G |
| Encode / Decode |   |   |   |   |   |   |   |   |
| Md | 2 | 2 | 1 |   |   | 2 |   | 1 |
|  | 1 | 1 | 2 |   | 2 | 1 | 1 | 2 |
|  | 0 | 0 | 0 | — | 1 | 0 | 2 |   |
|  |   |   |   |   | 0 |   | 0 | 0 |

For each position i, the first two bases in the indexDNA sequence are represented by d=[i−2, i−1]. When d ∈ set D={AT, CT, TT, CA, AA, CC, GG}, the base type of position i is constrained by d, and when d ∉ set D, the base type of position i is not constrained by d Taking d=[A,T] as an example, the case corresponds to Column No. 0 in the algorithm table. ATG is an initiation codon sequence and cannot appear in the indexDNA sequence, therefore, the site cannot be encoded to and the number of elements of the candidate base set Sd becomes 3, which are A, T, and C, respectively. The conversion algorithm in this case is designed to be 2=A, 1=T, and 0=C. When d=[T,T], the case corresponds to Column No. 2 in the algorithm table. At this point, the number of elements of the alternative base set Sd is reduced to 2, but 3 kinds of information need to be stored at the site. Under the constraint that the number of digits of the index DNA sequence is constant, one base must be added back in this case. If T is added back, a single-base repetitive sequence may be introduced, and if G is added back, an initiation codon sequence may be introduced. After weighing the results that may be caused by the two methods, it is necessary to preferentially avoid the generation of the initiation codon sequence, so base T is selected as the third element in the alternative base set. Finally, the conversion algorithm in this case is designed to be 0=C, 1=A, 2=T. Another special case is that, when d=[C,A], the case corresponds to Column No. 3 in the algorithm table, and only one base C remains in the alternative base set Sd. In this case, adding any base back will introduce the initiation codon, and at the same time, under the constraint of the condition that the length of the indexDNA sequence is constant, the information cannot be stored in this case. Therefore, an additional design is added to ensure -CA- sequence does not appear in the indexDNA sequence. This design corresponds to Column No. 6 in the algorithm table. When the second element of d is base C, the conversion algorithm is designed to be 0=G 1=T, 2=C, which avoids the generation of a CA sequence. In addition, when d∉D, this case corresponds to Column No. 7 in the algorithm table, and 0, 1, and 2 are stored by G, A, and T, respectively, thereby reducing the frequency of occurrence of base C. The first two bases are encoded according to the conversion algorithm of Column No. 7 in the figure, that is, G=0, A=1, and T=2.

Based on the above algorithm, the 15-digit ternary number sequence will be encoded from the first digit into a 15-digit indexDNA sequence, and the information of each digit of the two sequences will be in one-to-one correspondence, and finally the desired indexDNA is generated.

(2) Restoration Algorithm for indexDNA Sequence

Figure 4:
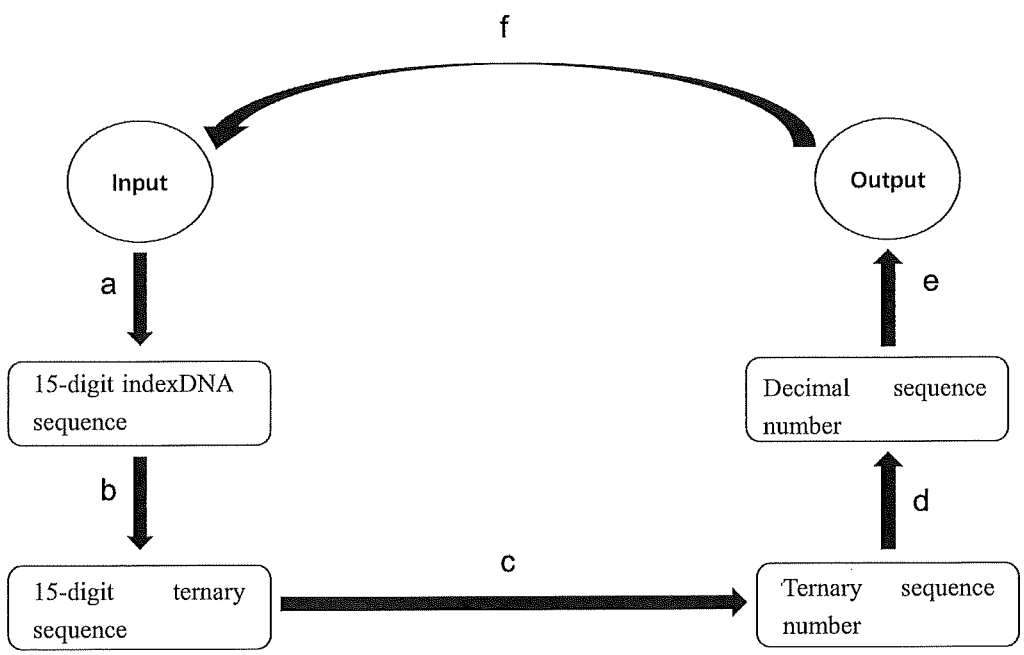
FIG. 4 shows a restoring process of an indexDNA sequence.

The restoration of an indexDNA sequence, that is, the decoding of an index DNA sequence is an inverse process of the above encoding process, as shown in FIG. 4.

The module begins with obtaining a fragment of data DNA sequence from the program. First, the indexDNA sequence with a length of 15 nt at the head end is extracted from the entire sequence (as shown in the process a in FIG. 4); then the indexDNA sequence is decoded according to the indexDNA sequence and ternary number sequence conversion algorithm to a 15-digit ternary number sequence (as shown in the process b in FIG. 4); after that, the ternary number sequence is degenerated into ternary sequence numbers (as shown in the process c in FIG. 4); the ternary numbers are further decoded into decimal sequence numbers N (as shown in the process d in FIG. 4), and the core of the algorithm of restoring ternary numbers to decimal numbers is N=Σ(Xi*3i), where X represents the ternary number of the i-th position, i represents the site, and i is taken from 0. Finally, the decimal sequence numbers N are output, and the string data obtained by the dataDNA sequence synchronously decoded from the data DNA sequence is stored at the Nth position of the data array. The program receives a new fragment of data DNA sequence to enter next cycle (as shown in the process e/f process in FIG. 4).

Similarly, the core of the above process is the process of decoding the 15-digit indexDNA sequence to the 15-digit ternary number sequence, and its algorithm design is shown in Table 1 Similar to the indexDNA sequence encoding process, when decoding, the first two bases are decoded according to the conversion algorithm of Column No. 7 in the figure, that is, G=0, A=1, T=2; when the base of the i-th site in the indexDNA sequence is converted into the ternary number of the i-th site in the ternary number sequence, it is constrained by the base sequence d=[i−2, i−1]. Different d sequences determine different conversion algorithms taken at the position i. So similarly, when the base of the i-th position is decoded, d=[i−2, i−1] is first judged; when d E set D={AT, CT, TT, CA, AA, GG CC, GC, TC, AC}, the decoding algorithm is performed according to Column No. 7 in the figure, that is, G=0, A=1, T=2; and when d ED, according to the specific sequence of d, the conversion algorithm in the corresponding column is taken for decoding.

Figure 5:
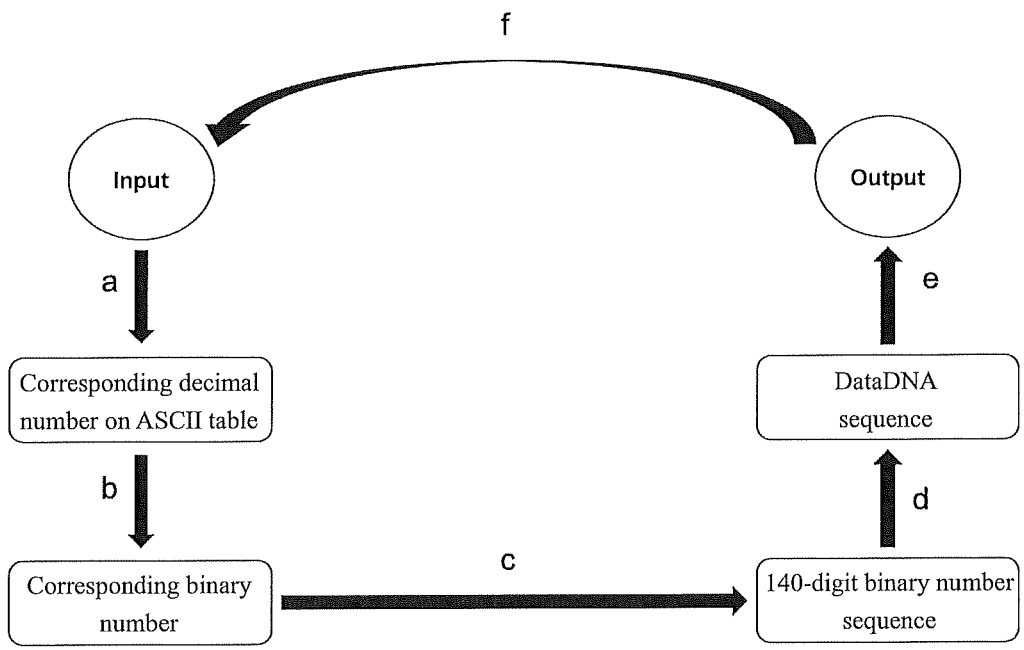
FIG. 5 shows a generating process of a dataDNA sequence.

Generation and Restoration of dataDNA Sequence (1) Generation Algorithm for dataDNA Sequence The dataDNA sequence is generated by using every 20 characters in the string sequence as a conversion unit, and each dataDNA sequence stores information of 20 characters. FIG. 5 shows the process of generating a dataDNA sequence.

The encoding of a dataDNA sequence is started when a string sequence of 20 characters is input inside the algorithm. First, each character is converted into a corresponding decimal number of the character on the ASCII code table (as shown in the process a in FIG. 5); then, each of the obtained decimal numbers is sequentially converted into a corresponding binary number format, where the conversion algorithm can call the internal function of the operating system, and the generated binary numbers start with "0b" (as shown in the process b in FIG. 5); after that, each binary number is sequentially converted into a 7-digit binary number sequence, where the algorithm of this process is to sequentially fill the numbers after "0b" in the 7-digit binary number sequence with an initial value set to "0000000" and then sequentially connect the 7-digit binary number sequences obtained from all 20 decimal numbers to form a 140-digit binary number sequence (as shown in the process c in FIG. 5); and then according to the binary number sequence and dataDNA sequence conversion algorithm, the 140-digit binary number sequence is converted into a dataDNA sequence (as shown by the process d in FIG. 5); finally, the dataDNA sequence is output to proceed to next step, and the variables in the module are returned to their initial values, to wait for the input of next string conversion unit.

The core of the above process is the process of converting the 140-digit binary number sequence to a dataDNA sequence (as shown in the process d in FIG. 5), and its algorithm design is shown in Table 2.

TABLE 2 dataDNA sequence conversion algorithm

| d | AT | CT | TT | CA | AA | GG | CC | X2/B |
|---|----|----|----|----|----|----|----|------|
| Number of Sd elements | 3 | 3 | 2 | 1 | 3 | 3 | 3 | 4 |
| Sd | A | A | A |   |   | A | A | A |
|    | T | T |   |   | T | T | T | T |
|    | C | C | C | C | C | C |   | C |
|    |   |   |   |   | G |   | G | C |
| Encode |   |   |   |   |   |   |   | Decode |
| Md | 0 | 0 | 0 |   |   | 0 | 0 | 00 |
|    | 10 | 10 |   |   | 0 | 10 | 10 | 01 |
|    | 11 | 11 | 1 | — | 10 | 11 |   | 10 |
|    |   |   |   |   | 11 |   | 11 | 11 |

The conversion of a dataDNA sequence follows the "quaternary-like" algorithm described above, and each site of the dataDNA sequence stores information of a 2-digit binary number sequence, except in a few cases Similar to the generation of an indexDNA sequence, the encoding of the dataDNA sequence shall also prevent the occurrence of an initiation codon sequence and single-base repetitive sequences. Therefore, it is necessary to avoid the sequences in the set S={ATG, CTG, TTG, CAT, CAG CAA, AAA, TTT, CCC, GGG}, and the sequence appearing in the set D={AT, CT, TT, CA, AA, GG CC} becomes a constraint for next site. The first two bases of the dataDNA sequence are encoded according to the algorithm in the case of X2\B. At this point, the number of elements of the alternative base set Sd is 4, which is not constrained by any condition, that is, 4-digit binary number sequence is stored in a 2-digit dataDNA sequence according to the rule of 00=A, 01=T, 10=C, 11=G In the subsequent sequences, when the base of the i-th site is encoded, the sequence value of d=[i-2, i-1] is first judged. If d∉D, the encoding is still performed according to the algorithm in the case of X2\B; if d∈D, the encoding of the i-th site will be constrained by d: if d=AT or CT or GG the number of elements of the alternative base set is 3, the alternative bases are A, T, C, and only these three kinds of information can be stored, so the conversion rule is degraded from complete quaternary to "quaternary-like" and the encoding is performed according to the rule of 0=A, 10=T, 11=C; if d=AA, the analysis process is the same as above, and the conversion rule becomes 0=T, 10=C, 11=G; if d=CC, the analysis process is the same as above, and the conversion rule becomes 0=A, 10=T, 11=G; if d=TT, the number of elements of the alternative base set is 2, the alternative bases are A, C, and only two kinds of information can be stored, so the conversion rule is degraded from complete quaternary to binary, and the encoding is performed according to the rule of 0=A, 1=C; if d=CA, the number of elements of the alternative base set is 1, and the alternative base is only C and is unable to store the information of a binary site, so in this case, the base C does not store any information, and is simply used as the site-holding base to be encoded at the site i.

On the basis of the above conversion algorithm, in order to improve the security of data storage, a certain encryption function is added. In the encryption algorithm, the design of the conversion rule is still as shown in Table 2, except that the bases in the alternative bases set Sd are no longer sequenced in a constant manner, but sequenced randomly in each column, so that the conversion rule is expanded from 1 to 6*6*4*1*6*6*6*24=373, 284. The user applies for a randomly generated conversion rule by user name and password when bio-storing the data, and the data restoration can only be realized when the right rule is obtained by providing the user name and password.

Since the above algorithm is a hybrid of binary and quaternary conversion, it is very likely that two sites at the ends of the binary number sequence cannot be encoded (for example, only one site 1 is left in the binary number sequence, and this case is not in the corresponding conversion algorithm). Therefore, for the last conversion of the end, the algorithm shown in Table 3 is used instead. The two-digit base sequence in the algorithm table does not form an initiation codon sequence, regardless of which base is attached to both ends. So far, the 20 characters in the string text have been encoded as a dataDNA sequence to be stored therein, the sequence enters next module of the program and is further processed, and the module receives a new converted text.

TABLE 3

Binary number sequence end conversion algorithm

|  | DNA sequences | | | | | |
| --- | --- | --- | --- | --- | --- | --- |
|  | AC | TC | CG | GA | GT | GC |
| Binary number sequences | 0 | 1 | 00 | 01 | 10 | 11 |

(2) Restoration Algorithm for dataDNA Sequence

Figure 6:
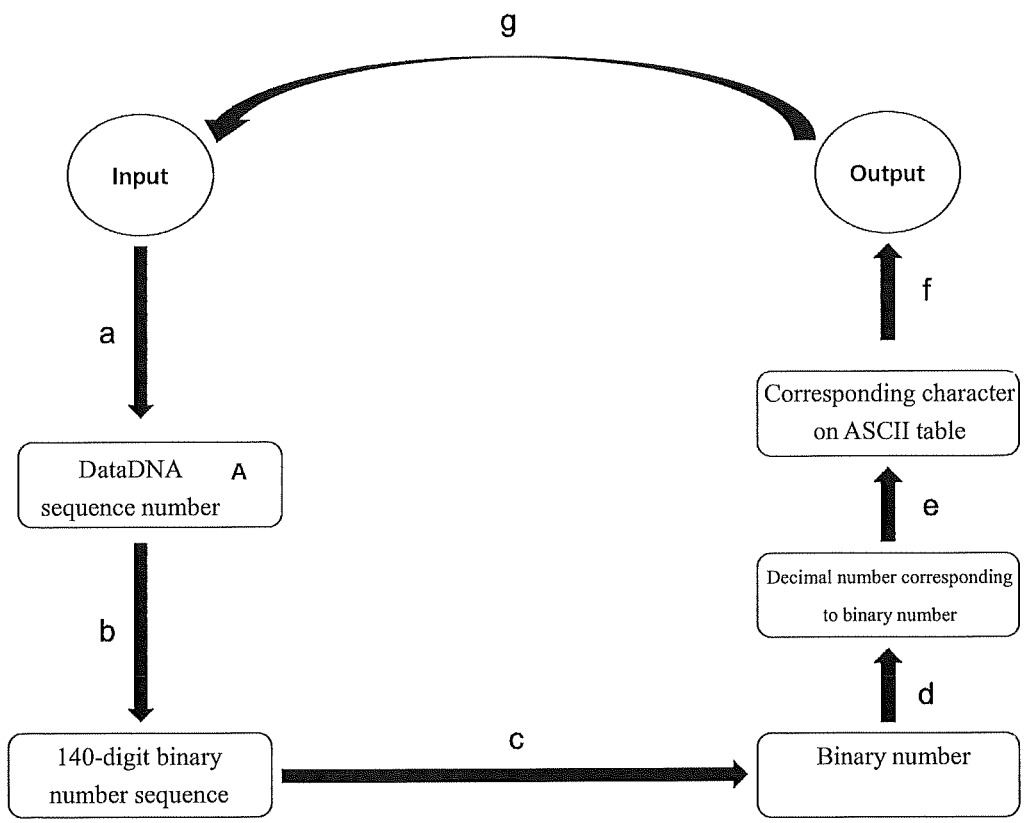
FIG. 6 shows a restoring process of a dataDNA sequence.

The decoding of a dataDNA sequence is a restoration process of the above process. The program design flow is shown in FIG. 6. The module begins with inputting a fragment of data DNA sequence to the program and captures a dataDNA sequence therein, i.e., the part of [17:47] in the data DNA sequence (as shown in the process a in FIG. 6); then the dataDNA sequence is decoded into a 140-digit binary number sequence by a conversion algorithm between dataDNA sequences and binary number sequences (Table 2) (as shown in the process b in FIG. 6); this 140-digit binary number sequence is actually a sequence of twenty 7-digit binary number sequences connected, and the 7-digit binary number sequences are now separated from each other and sequentially restored to binary numbers stored in respective sequences (as shown in the process c in FIG. 6); a binary number identifier "0b" is added to each binary number, and the internal function of the system is called to decode the binary number into a decimal number (as shown in the process d in FIG. 6); the corresponding characters of the decimal numbers in the ASCII table are sequentially written by the internal function of the system (as shown in the process e in FIG. 6); finally, the 20 characters in order constitute a 20-byte string, the string is output from the module, and all variables of the module are returned to their initial state (as shown in the process f/g in FIG. 6.)

The process of decoding the dataDNA sequence into a 140-digit binary number sequence is the core of the module, and its algorithm design is shown in Table 2. The decoding process is still constrained by the elements in the sequence set D={AT, CT, TT, CA, AA, GG CC}. The first two bases of the dataDNA sequence are decoded according to the rule of the column X2 \B in the table, that is, A=00, T=01, C=10, G=11; then, when the base at the i-th position in the dataDNA sequence is decoded, the sequence of d[i-2, i-1] is first judged, where if d E D, the conversion algorithm is as above; if d ED, the decoding process is constrained by sequence d, and the decoding is performed according to the conversion rules in the vertical columns of different sequences d in the table; the case of d=CA is specifically described, where the base C of the i-th position only functions as a placeholder, does not store any information, and therefore does not restore any content; the above process is stopped at the last two bases of the dataDNA sequence, and the two bases at the end are decoded according to Table 4.

TABLE 4

Conversion algorithm of two bases at the end of dataDNA sequence

|  | DNA sequences | | | | | |
| --- | --- | --- | --- | --- | --- | --- |
|  | AC | TC | CG | GA | GT | GC |
| Binary number sequences | 0 | 1 | 00 | 01 | 10 | 11 |

Generation and Restoration of correctionDNA Sequence
(1) Generation Algorithms for correctionDNA Sequence To improve the fidelity of data storage and avoid the loss or distortion of data during storage is an important prerequisite for biological storage of data. Since the design of the conversion algorithm leads to high dependence between adjacent bases of the dataDNA sequence, once the base at a site is mutated, the decoding of the entire dataDNA sequence may be affected. Thus, an algorithm is designed to generate a correctionDNA sequence that can be used to assess whether a data DNA sequence is mutated and can help to restore a single base mutation occurring at a site.

The correctionDNA consists mainly of two parts, a preliminary judgment sequence of 4 nt in length and a deep judgment sequence of 10 nt in length. The function of the preliminary judgment sequence is to determine the type of a single base mutation in the sequence (base substitution or base deletion or base insertion), and to determine the kind of single base of the mutation (substitution occurs between which two kinds of base or insertion or loss occurs in which kind of base); the function of the deep judgment sequence is to judge the site of the mutation and the specific mutation based on the results obtained by the preliminary judgment sequence. After the mutation is corrected, the sequence can be restored to the raw sequence.

The generation algorithm for the preliminary judgment sequence relies on a mathematical function:

$$X(i)=(-1)^{N(i)}$$

Wherein i=A, T, C, G; N(i) is the number of base i present in the indexDNA sequence and dataDNA sequence;

The 4-digit base at one end of the correctionDNA sequence sequentially stores the X(i) values when i=A, T, C, and G Since the value of X(i) is only 1 or −1, the base C is used to store −1 and the base G is used to store 1. Thus, the preliminarily judgment sequence has been formed, which is a sequence consisting of only G and C located at the 4th position of the end of the correctionDNA sequence.

Taking the sequence -ATGCTTCGACGTCGAG- (SEQ ID NO: 1) as an example, the generation of the preliminary judgment sequence is demonstrated. First, calculated separately are:

$$X(A)=(-1)^{N(A)}=(-1)^3=-1;$$

$$X(T)=(-1)^{N(T)}=(-1)^4=1;$$

$$X(C)=(-1)^{N(C)}=(-1)^4=1;$$

$$X(G)=(-1)^{N(G)}=(-1)^5=-1;$$

The preliminary judgment sequence is CGGC;
The generation algorithm for the deep judgment sequence relies on a mathematical function:

$$sum = \sum_{i=1}^{N} val(i) * position(i)$$

Wherein i=A, T, C, G; val(i) is the value of base i, as shown in Table 5; position(i) is the position coordinate of the base i; N is the total length of the indexDNA sequence and dataDNA sequence;

TABLE 5

Assignment table of various bases in the error correction mechanism

| i | A | T | C | G |
|---|---|---|---|---|
| val(i) | 1 | 2 | 3 | 4 |

Each fragment of data DNA sequence generates a sum of decimal numbers. The decimal numbers are converted into ternary numbers, the ternary numbers are transmitted to a 10-digit ternary number sequence, and then the 10-digit ternary number sequence is converted according to the indexDNA sequence conversion algorithm (algorithm for conversion between ternary number sequences and DNA sequences, Table 1). To prevent the appearance of the initiation codon sequence at the junction of the two parts, a protection base C is added between them. Finally, a 15 nt correction sequence is generated, and connected to the end of the data DNA sequence, to generate a complete data DNA sequence including indexDNA, dataDNA and correctionDNA.

Taking the sequence -ATGCTTCGACGTCGAG- (SEQ ID NO: 1) as an example, the generation of the deep judgment sequence is demonstrated. First calculated is:

$$sum=\sum_{i=1}^{N}val(i)*position(i)=1*1+2*2+3*4+4*3+5*2+6*2+7*3+8*4+ \ldots +16*4=385$$

Then, the sequence is converted into a 10-digit ternary number sequence: 0000112021; then the 10-digit ternary number sequence is converted into a 10-digit deep judgment sequence according to the algorithm for conversion between ternary number sequences and DNA sequences in the indexDNA generation module: GGCGAATCCT (SEQ ID NO: 2).

The protection base C is added at the junction between the preliminary judgment sequence and the deep judgment sequence, and the correctionDNA sequence is CGGCcGGCGAATCCT (SEQ ID NO: 3).

(2) Restoration Algorithm for correctionDNA Sequence

The module begins with inputting a fragment of data DNA sequence into the program. The module first captures the correctionDNA sequence at the end of the data DNA sequence, and restores the preliminary judgment sequence to a judgment sequence consisting of 1 and −1 and also having four digits which respectively store the base number judgment values in the raw data DNA sequence; and simultaneously, the module restores the 10 nt deep judgment sequence to a decimal number (the algorithm for the process is completely similar to the restoration of the indexDNA sequence, and will not be described again), the decimal number represents a base bitwise weighted sum of the DNA sequence of raw data.

On the other hand, the indexDNA and dataDNA portions of the data DNA received by the module are calculated using the preliminary judgment function and the deep judgment function, to obtain a base number judgment value and a base bitwise weighted sum of the existing data DNA sequence; the calculation results of the existing data DNA sequence are compared with those of the raw data DNA restored from the correctionDNA sequence. That is, entire information is obtained, including whether or not a mutation occurs, which kind of base has which type of mutation, and which site the mutation occurs; further, the mutated base is restored to obtain the same sequence as the raw DNA sequence, and accurate data restoration can be performed.

Taking the storage of -ATGCTTCGACGTCGAG- (SEQ ID NO: 1) as an example, three types of mutations including deletion, insertion and substitution are respectively introduced to further describe the operation of an error correction mechanism. The correctionDNA sequence has been generated and connected to the end of the above sequence, so the stored sequence is -ATGCTTCGACGTCGAGgcCGGCcGGCGAATCCT (SEQ ID NO: 4).

1) Base substitution: -ATCCTTCGACGTCGAGgcCGGCcGGCGAATCCT (SEQ ID NO: 5) (the third position of the sequence is mutated from G to C during storage).

The mutated sequence ATCCTTCGACGTCGAGgcCGGCcGGCGAATCCT (SEQ ID NO: 5) is obtained after sequencing. First, the correctionDNA sequence is restored to obtain:

$$X(A)=-1; X(T)=1; X(C)=1; X(G)=-1; \Sigma=385$$

Then, preliminary and deep judgments are made to the dataDNA to obtain:

$$X'(A)=-1; X'(T)=1; X'(C)=-1; X'(G)=1; \Sigma'=382$$

Since the values of X(C) and X(G) have changed, it is determined by the preliminary judgment that base substitution occurs between C and G bases.

Then, according to the formula:

$$position = \frac{|\Sigma - \Sigma'|}{val(G) - val(C)}$$

The mutation site is |382−385|/(4−3)=3. According to it can be judged that G is mutated to C. Therefore, in the end, it is determined that the third base in the dataDNA sequence is mutated from G to C. This site is restored to obtain the raw sequence.

2) Base insertion: -ATGC-TATCGACGTCGAGgcCGGCcGGCGAATCCT (SEQ ID NO: 6) (an A is added after the fifth base of the sequence)

The mutated sequence -ATGC-TATCGACGTCGAGgcCGGCcGGCGAATCCT (SEQ ID NO: 6) is obtained after sequencing. First, the correctionDNA sequence is restored to obtain:

$X(A)=-1;X(T)=1;X(C)=1;X(G)=-1;\Sigma=385$

Then, preliminary and deep judgments are made to the dataDNA to obtain:

$X'(A)=1;X'(T)=1;X'(C)=1;X'(G)=-1;\Sigma'=422$

Since only the value of X(A) changes, it can be inferred from the preliminary judgment that insertion or deletion of the base A has occurred. Then, based on the result of deep judgment E'>E, it is further determined that the insertion of the base A has occurred. Starting from the first base A of the mutated sequence, the base A at each position is deleted, and then E' is calculated. When the sum after A at a certain position is deleted is equal to 385, the insertion site is found. The insertion site is removed to obtain the raw sequence.

3) Base deletion: -ATGCTT-GACGTCGAGgcCGGCcGGCGAATCCT (SEQ ID NO: 7) (one base C is lost between the sixth and seventh bases in the sequence)

The mutated sequence -ATGCTT-GACGTCGAGgcCGGCcGGCGAATCCT (SEQ ID NO: 7) is obtained after sequencing. First, the correctionDNA sequence is restored to obtain:

$X(A)=-1;X(T)=1;X(C)=1;X(G)=-1;\Sigma=385$

Then, preliminary and deep judgments are made to the dataDNA to obtain:

$X'(A)=-1;X'(T)=1;X'(C)=-1;X'(G)=-1;\Sigma'=338$

Since only the value of X(C) changes, it can be inferred from the preliminary judgment that insertion or deletion of the base C has occurred. Then, based on the result of deep judgment $\Sigma'<\Sigma$, it is further determined that the deletion of the base C has occurred. Therefore, a base C is added to each site from the first site of the mutated sequence, and E' is calculated. When the sum after a certain C has been added is equal to 385, the deletion site is found, and the raw sequence is obtained by adding C to this site.

Figure 7:
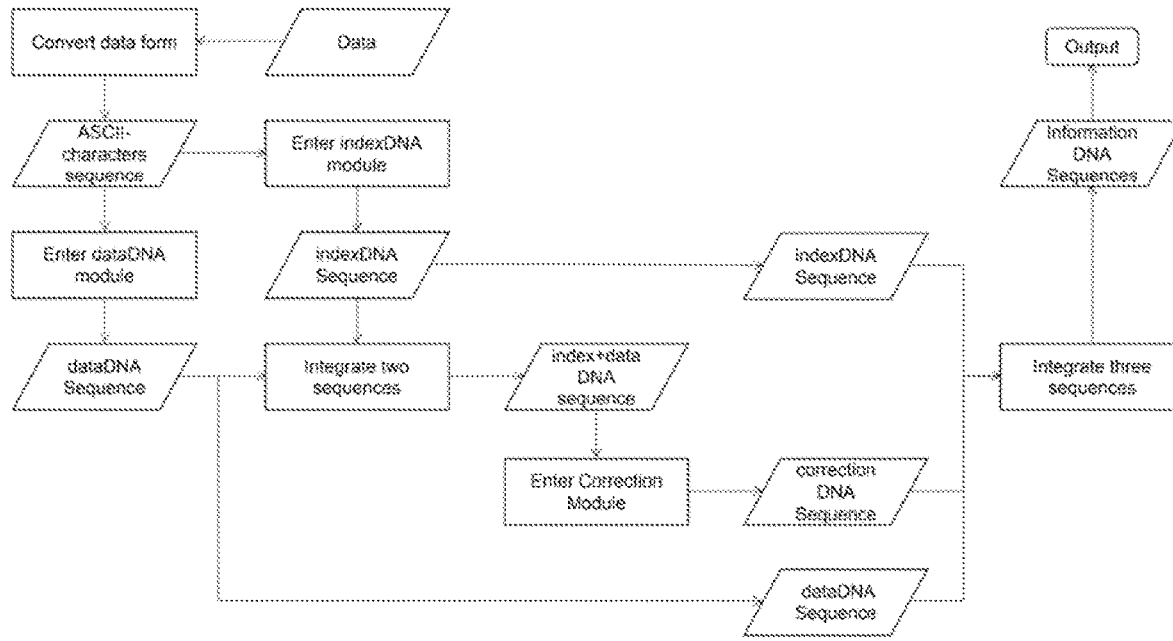
FIG. 7 is a schematic diagram of the generation of a complete data DNA sequence.

Generation and Restoration of Complete Data DNA Sequences (1) Generation of Complete Data DNA Sequence Different types of data are preprocessed before entering the conversion program, images or texts or audio data are first converted into a "string text" format, and the contents of the file are saved in a txt format. This txt text is the object operated by the biological converter. FIG. 7 is a schematic diagram of the generation of complete data DNA sequences.

The data text is converted to a data DNA sequence by using 20 characters as a conversion unit. First, the indexDNA generation module generates an indexDNA sequence identifying the sequence number information; at the same time, the string sequence is input into the dataDNA generation module to generate a dataDNA sequence storing the string information of the unit; then, the indexDNA sequence is connected with the dataDNA sequence to form an index+dataDNA sequence, and the index+dataDNA sequence is input to the correctionDNA generation module to generate a correctionDNA sequence; finally, the three sequences of indexDNA, dataDNA, and correctionDNA are connected end to end to form a complete data DNA sequence. After that, the entire program accepts next 20-byte string conversion unit, and so on until all the txt texts are converted into data DNA sequences, and a data DNA sequence library storing all information of the raw data is obtained.

When the three module sequences are connected into a data DNA sequence, in order to avoid the formation of an initiation codon sequence between the end base of the previous module and the first base of the latter module, a 2 nt protection sequence is added to each of the two connection sites. After the characteristics of the elements in the set of all initiation codon sequences are inspected, it is found that the CG sequence does not generate an initiation codon regardless of the kind of base added before or after. Therefore, the sequence is selected as the protection sequence. A complete data DNA sequence is finally generated, including a 15 nt indexDNA fragment, a 15 nt correctionDNA fragment, an approximately 100 nt dataDNA fragment, and two 2 nt protection sequences.

(2) Restoration of Complete Data DNA Sequences

Figure 8:
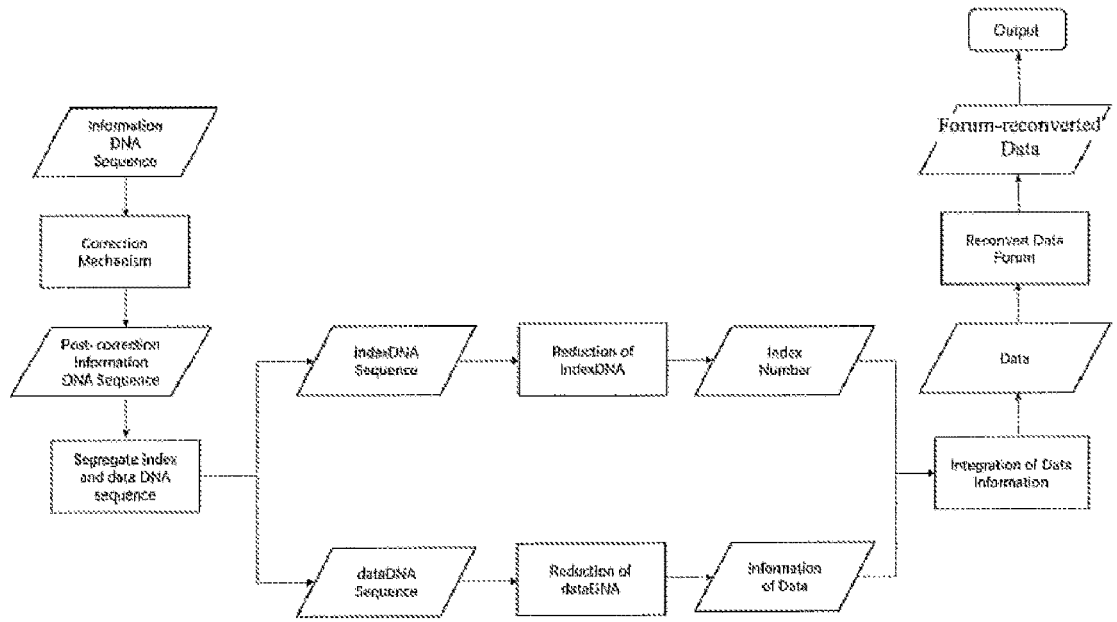
FIG. 8 is a schematic diagram of the restoration of a complete data DNA sequence.

FIG. 8 is a schematic diagram of the restoration of complete data DNA sequences. The data DNA sequence library stored in the data DNA cell bank is sequenced and saved in a txt format. Each line in the text represents a fragment of data DNA sequence, and the data DNA sequences at this time are arranged disorderly. When the data is restored, the conversion software starts to capture from the first line of the text. The complete data DNA sequence first enters the correction module and is assessed by the error correction mechanism, and the indexDNA sequence and the dataDNA sequence therein are restored. After the error-corrected data DNA sequence is obtained, the program captures the indexDNA sequence and the dataDNA sequence therein into the index module and the data module for restoration respectively. The former restores the sequence number corresponding to the fragment of data DNA, and the latter restores the data stored in this fragment of data DNA, that is, a 20-byte character string; then, the character string is stored in the data generation text corresponding to the sequence number, and the converter captures a sequence of next line in the text, and so on. Finally, text data consisting of the strings in the ASCII table is obtained, and then later data format conversion is performed to obtain restored final data.

Example 2. Algorithm Test and Results

Based on the above algorithms and designs, a simple bio-converter was written, and the performance of this converter was tested.

(1) Storage of Small-Scale Text Data

The first-generation converter did not have index and correction modules, so only some very short texts can be converted. In the case of dealing with some short texts, since there are no indexDNA sequences and correctionDNA sequences, data DNA sequences are shortened, the efficiency is improved, and the cost is reduced at the application level. On the other hand, in the short term, the current situation of bio-storage of short texts is more common. Taking "Dai Lab, Tsinghua University, Synthetic Yeast, Synthetic Biology" as test texts, they are converted into dataDNA sequences as shown in Table 6:

TABLE 6

Storage test results of small-scale text data

| Text for Testing | dataDNA Sequence | Information of dataDNA Sequence | Reduction of Text |
| --- | --- | --- | --- |
| Dai Lab | TATACACCACGAAGCCACCTAATTAGAGA AGCACCACCACTAC (SEQ ID NO: 8) | Number of Bases: 43 Content of G/C: 0.47 | Dai Lab |
| Tsinghua University | TATACCTAGCTCCTAGCGCGAGGTCACGC CGCACTACACACCTTCGTGTCCACGGAGT CTAGGATAGCTCCTAGGACTCCACCTATAC (SEQ ID NO: 9) | Number of Bases: 88 Content of G/C: 0.56 | Tsinghua University |
| Synthetic Yeast | TATACCACGGCACGCGCGCCACGTATTAC GGACTTCACGCACGTAATTCCACGCTAGC ACTCCACGGTCACCACTAC (SEQ ID NO: 10) | Number of Bases: 77 Content of G/C: 0.57 | Synthetic Yeast |
| Synthetic Biology | TATACCACGGCACGCGCGCCACGTATTAC GGACTTCACGCACGTAATTAACGTAGCGG CTTAGTGGTTCGGTTACAGT (SEQ ID NO: 11) | Number of Bases: 78 Content of G/C: 0.53 | Synthetic Biology |

Figure 9:
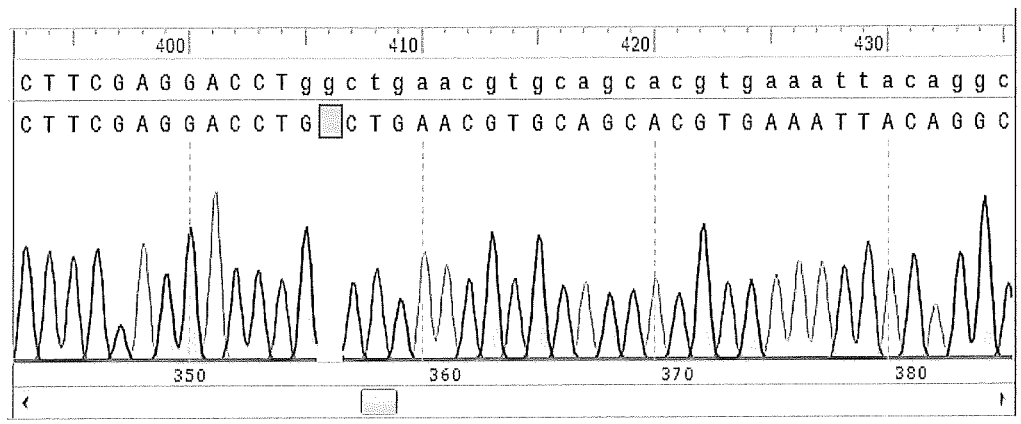
FIG. 9 shows a result of sequencing of DNA fragments storing data extracted from cells.

The above dataDNA sequences were converted into yeast, stored in a plasmid form or integrated into genomes for testing, and subcultured. After 100 generations, these fragments were extracted and sequenced, the dataDNA sequences obtained by sequencing were basically the same as the initial state, and only one set integrated into the genomes showed a single base loss, as shown in FIG. 9. This also verifies the necessity to add error correction mechanisms later.

(2) Test of Encryption Mechanism

The encryption mechanism was introduced in the second-generation converter and tested with the text "Hello, World!", as shown in Table 7. With different user names and passwords, the same text generated different dataDNA sequences. In the restoration of dataDNA sequences, it is also necessary to provide correct user names and passwords to implement decoding, so that higher security and confidentiality are obtained for user data.

(2) Conversion Test of Large-Scale Data (KB Level)

Figure 10:
FIG. 10 shows the emblem of Tsinghua University.

The third-generation bio-conversion software is mainly designed for large-scale data storage tasks. In the third-generation program, an index module and a correction module were added. In order to test its performance, the emblem of Tsinghua University (shown in FIG. 10) with a size of 24 kB and the song lyrics of Tsinghua University were used as test objects for conversion.

Figure 11:
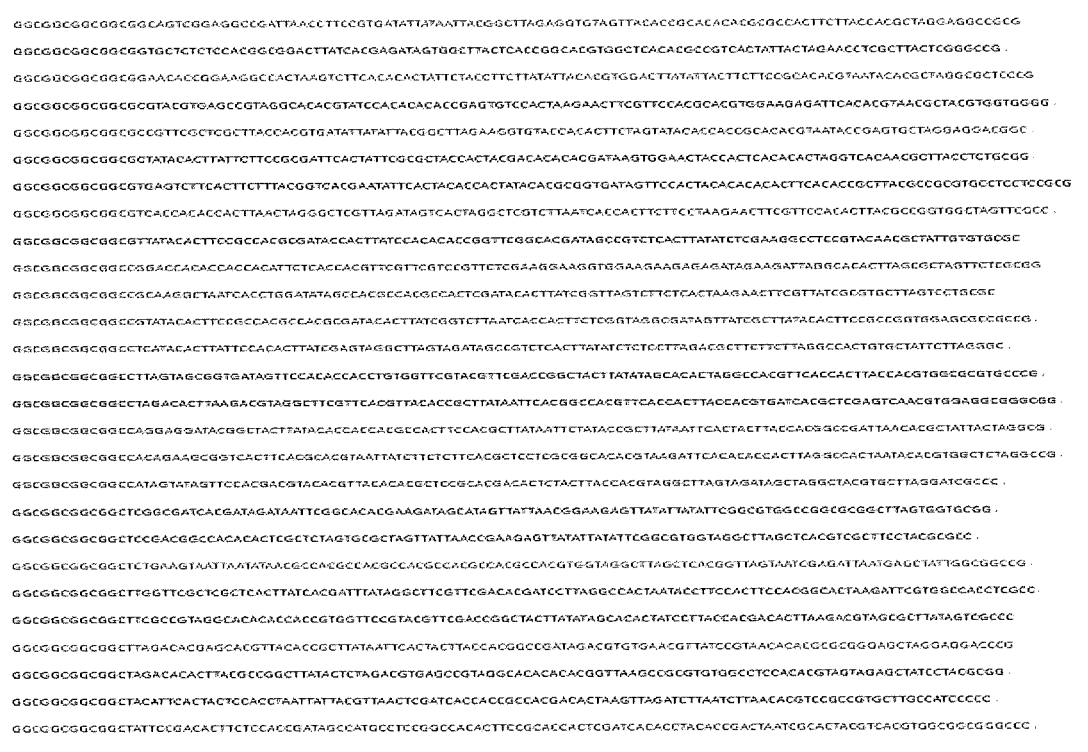

The third-generation bio-converter was used to convert the image and lyrics into a data DNA library containing 1084 data DNA sequences. The positions of the sequences in the library were artificially disturbed, and single base mutation was randomly introduced into part of the data DNA sequences, to simulate a genuine biological storage process, as shown in FIG. 11. By restoring the data DNA sequence library, the raw image data and text data can be finally obtained.

TABLE 7

Test text and results of encryption mechanism

| Text for Testing | Username and Password | dataDNA Sequence | Reduction of Text |
| --- | --- | --- | --- |
| Hello, World! | username: user1 password: ******* | TGCGTGGAGTGTACACGATTCTCGCCTTCG AACACACACTCTAGTGTGCGCCTC (SEQ ID NO: 12) | Hello, World! |
| Hello, World! | username: user2 password: ******* | GATTAGAAGAGAGCTCACCTTAGTGTTAAT CCTCCACGAACCGAGATTATTGA (SEQ ID NO: 13) | Hello, World! |
| Hello, World! | username: user3 password: ******* | GTCTTCGAGACACTTCACTCGGTCTACCTT AATCACACACGTTATTCACCTATCCGA (SEQ ID NO: 14) | Hello, World! |
| Hello, World! | username: user4 password: ******* | GCACCACCTTCCACCACTCCACTTAGTACA CACCTATTCCGTTACCACTCCACCTCCTCAT C (SEQ ID NO: 15) | Hello, World! |

The invention claimed is:

1. A method for converting data into data DNA sequences including mutation correction sequences, comprising dividing the data into one or more data conversion units, providing a binary number sequence of each data conversion unit, and converting each data conversion unit into a data DNA sequence including a mutation correction sequence according to the following steps, thus acquiring a DNA sequence library; wherein the DNA sequence library contains one or more data DNA sequences, and each data DNA sequence is converted from a data conversion unit; wherein the steps comprises:

(1) converting a binary number sequence of a data conversion unit into a preliminary data DNA sequence without a mutation correction sequence, the preliminary data DNA sequence including data content information of the data conversion unit;

(2) first, generating a preliminary judgment sequence of 4 bases based on the preliminary data DNA sequence: calculating base number judgment values X(i) when i=A, T, C, G according to the following formula:

$$X(i) = (-1)^{N(i)}$$

wherein i=A, T, C, G; N(i) is the number of base i present in the preliminary data DNA sequence;

storing the base number judgment values X(i) when i=A, T, C, G using the 4 bases in the preliminary judgment sequence respectively, and storing −1 and 1 using bases C and G, respectively, to generate a preliminary judgment sequence;

then, based on the preliminary data DNA sequence, generating a deep judgment sequence of 10 bases: calculating a base bitwise weighted sum of the preliminary data DNA sequence according to the following formula:

$$\text{sum} = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;

converting the value of the base bitwise weighted sum into a 10-bit ternary number sequence to generate a deep judgment sequence;

connecting the preliminary judgment sequence and the deep judgment sequence, and adding a protection base C at the junction to obtain a correctionDNA sequence;

(3) connecting the preliminary data DNA sequence and the correctionDNA sequence, and adding a protection sequence of 2 bases in length at the junction to obtain a data DNA sequence including a mutation correction sequence.

2. The method of claim 1, wherein step (1) comprises:

(1-1) converting the position number of the data conversion unit in the data into a ternary number sequence with a fixed number of bits, and then converting the ternary number sequence into an indexDNA sequence according to an indexDNA sequence conversion rule, where the number of bases of the indexDNA sequence is the same as the number of bits of the ternary number sequence;

wherein the indexDNA sequence conversion rule is:

(a) for the i-th position in the indexDNA sequence, the two bases before this position are represented as d=[i−2, i−1];

(b) for the first two positions in the indexDNA sequence, the corresponding conversion between ternary numbers and bases is performed according to the correspondence corresponding with the condition d∉Set {AT,CT, TT,CA,AA,CC,GG} shown in the table below;

|  | Correspondence | |
| Conditions | Ternary numbers | Bases |
| --- | --- | --- |
| d = [A, T] | 0, 1, 2 | A, T, C |
| d = [C, T] | 0, 1, 2 | A, T, C |
| d = [T, T] | 0, 1, 2 | A, T, C |
| d = [A, A] | 0, 1, 2 | T, C, G |
| d = [G, G] | 0, 1, 2 | A, T, C |
| d ∈ Set{CC, GC, TC, AC} | 0, 1, 2 | T, C, G |
| d ∉ Set{AT, CT, TT, CA, AA, CC, GG} | 0, 1, 2 | G, A, T |

(c) starting from the third position in the indexDNA sequence, the conversion is conducted in turn according to the rules shown in the table above by: first, judging which condition in the table the i-th position satisfies, and then performing the corresponding conversion between the ternary number and the base at the i-th position according to the correspondence corresponding with the condition;

(1-2) converting the binary number sequence of the data conversion unit into a dataDNA sequence according to a dataDNA sequence conversion rule;

wherein the dataDNA sequence conversion rule is:

(a) for the i-th position in the dataDNA sequence, the two bases before this position are represented as d=[i−2, i−1];

(b) for the first two positions in the dataDNA sequence, the corresponding conversion between binary numbers and bases is performed according to the correspondence corresponding with the condition d∉Set {AT, CT, TT, CA, AA, GG, CC} shown in the table below;

|  | Correspondence | |
| Conditions | Binary numbers | Bases |
| --- | --- | --- |
| d = [A, T] | 0, 10, 11 | A, T, C |
| d = [C, T] | 0, 10, 11 | A, T, C |
| d = [T, T] | 0, 1 | A, C |
| d = [C, A]* | — | C |
| d = [A, A] | 0, 10, 11 | T, C, G |
| d = [G, G] | 0, 10, 11 | A, T, C |
| d = [C, C] | 0, 10, 11 | A, T, G |
| d ∉ Set{AT, CT, TT, CA, AA, GG, CC} | 00, 01, 10, 11 | A, T, C, G |

*wherein when d = [C, A], base C is at the i-th position, and the base C does not correspond to any binary number (c) starting from the third position in the dataDNA sequence, the conversion is conducted in turn according to the rules shown in the table above by: first, judging which condition in the table the i-th position satisfies, and then performing the corresponding conversion between the binary number and the base at the i-th position according to the correspondence corresponding with the condition;

(d) when the binary number sequence has only 1 or 2 positions left, the conversion between binary numbers and bases is performed using the rules shown in the table below;

|  | Bases | | | | | |
| --- | --- | --- | --- | --- | --- | --- |
|  | AC | TC | CG | GA | GT | GC |
| Binary number sequence | 0 | 1 | 00 | 01 | 10 | 11 |

(1-3) connecting the indexDNA sequence and the dataDNA sequence of the data conversion unit, and adding a protection sequence of 2 bases in length at the junction to obtain an index+dataDNA sequence as the preliminary data DNA sequence without a mutation correction sequence.

3. The method of claim 2, wherein in step (1-3), the correctionDNA is connected to one end of the dataDNA in the index+dataDNA sequence.

4. A method for converting encrypted data DNA sequences, comprising:

(1) providing a user name and a password, and randomly generating a corresponding mode between a specific binary number and a specific base in each set of correspondences in the dataDNA sequence conversion rule according to the user name and the password;

(2) converting data into data DNA sequences using the method for converting data into data DNA sequences including mutation correction sequences, the method comprising dividing the data into one or more data conversion units, providing a binary number sequence of each data conversion unit, and converting each data conversion unit into a data DNA sequences including a mutation correction sequence according to the following steps, thus acquiring a DNA sequence library; wherein the DNA sequence library contains one or more data DNA sequences and each data DNA sequence is converted from a data conversion unit; wherein the steps comprises:

(2-1) converting a binary number sequence of a data conversion unit into a preliminary data DNA sequence without a mutation correction sequence, the preliminary data DNA sequence including data content information of the data conversion unit;

(2-2) first, generating a preliminary judgement sequence of 4 bases based on the preliminary data DNA sequence: calculating base number judgement values $X(i)$ when i=A, T, C, G according to the following formula:

$$X(i)=(-1)^{N(i)}$$

wherein i=A, T, C, G; N(i) is the number of base i present in the preliminary data DNA sequence;

storing the base number judgment values $X(i)$ when i=A, T, C, G using the 4 bases in the preliminary judgement sequence respectively, and storing −1 and 1 using bases C and G, respectively, to generate a preliminary judgement sequence;

then based on the preliminary data DNA sequence, generating a deep judgment sequence of 10 bases; calculating a base bitwise weighted sum of the preliminary data DNA sequence according to the following formula:

$$\text{sum} = \sum_{i=1}^{N} val(i) * \text{position}(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;

converting the value of the base bitwise weighted sum into a 10-bit ternary number sequence to generate a deep judgement sequence, connecting the preliminary judgement sequence and the deep judgement sequence, and adding a protection base C at the junction to obtain a correctionDNA sequence;

(2-3) connecting the preliminary data DNA sequence and the correctionDNA sequence, and adding a protection sequence of 2 bases in length at the junction to obtain a data DNA sequence including a mutation correction sequence, wherein when the binary number sequence of each data conversion unit is converted into a dataDNA sequence according to the dataDNA sequence conversion rule, the specific binary number is converted into a corresponding specific base according to the corresponding mode generated in step (1).

5. The method of claim 1, wherein the method is implemented on a computer.

6. A method for correcting DNA sequences obtained by sequencing and restoring the same to data, comprising:

(1) providing DNA sequences obtained by sequencing, the DNA sequences comprising preliminary data DNA sequences and mutation correction sequences, wherein the preliminary data DNA sequence comprises data content information of a data conversion unit; wherein the preliminary data DNA sequence in the DNA sequences obtained by sequencing has at most one base mutation;

(2) based on each preliminary data DNA sequence, calculating a base number judgment value $X'(i)$ of the preliminary data DNA sequence according the following formula:

$$X'(i)=(-1)^{N(i)}$$

wherein i=A, T, C, G; N (i) is the number of base i present in the preliminary data DNA sequence;

comparing the base number judgment value $X'(i)$ of the preliminary data DNA sequence with the base number judgment value $X(i)$ obtained by restoration of the preliminary judgment sequence in the mutation correction sequence included in the DNA sequence obtained by sequencing according to the same rule:

if the base number judgment values of two bases change, it indicates that the preliminary data DNA sequence has a base substitution compared to the unmutated preliminary data DNA sequence, and the substitution is a substitution of one of the two bases by the other;

if only the base number judgment value of one base changes, it indicates that the preliminary data DNA sequence has insertion or deletion of this base compared to the unmutated preliminary data DNA sequence;

if none of the base number judgment values of bases changes, it indicates that the preliminary data DNA sequence has no mutation;

(3) based on the preliminary data DNA sequence, calculating a base bitwise weighted sum' of the preliminary data DNA sequence according to the following formula:

$$sum' = \sum_{i=1}^{N} val(i) * \text{position}(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;

comparing the base bitwise weighted sum' of the preliminary data DNA sequence with the base bitwise weighted sum obtained by restoration of the deep judgment sequence in the mutation correction sequence included in the DNA sequence obtained by sequencing according to the same rule;

in the case where the preliminary data DNA sequence has base substitution compared to the unmutated preliminary data DNA sequence: if sum'>sum, the base substitution is that the base having a smaller val(i) value is substituted by the base with a larger val(i) value; if sum'<sum, the base substitution is that the base having a larger val(i) value is substituted by the base with a smaller val(i) value; the position coordinate at which the base substitution occurs is the absolute value of the divisor obtained by dividing the difference between sum' and sum by the difference between the val(i) of the two bases; substituting the base at the position by the other of the two bases and correcting the sequence to an unmutated preliminary data DNA sequence;

in the case where the preliminary data DNA sequence has insertion or deletion of one base compared to the unmutated preliminary data DNA sequence;

if sum'>sum, it indicates that base insertion occurs, and the base insertion position is judged as follows: starting from the position where the base appears for the first time in the preliminary data DNA sequence, deleting the base at each position, and calculating a base bitwise weighted sum" of the preliminary data DNA sequence after deletion according to the following formula:

$$sum'' = \sum_{i=1}^{N} val(i) * \text{position}(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are deleted;

when the base bitwise weighted sum" calculated after the base at a certain position is deleted is equal to the base bitwise weighted sum obtained by restoration of the deep judgment sequence in the mutation correction sequence included in the DNA sequence obtained by sequencing according to the same rule, the position is the base insertion position; deleting the base at the position and correcting the sequence to an unmutated preliminary data DNA sequence;

if sum'<sum, it indicates that base deletion occurs, and the base deletion position is judged as follows: starting from the first position of the preliminary data DNA sequence, inserting the base to each position, and calculating a base bitwise weighted sum''' of the preliminary data DNA sequence after insertion according to the following formula:

$$sum''' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are inserted;

when the base bitwise weighted sum''' calculated after the base is inserted at a certain position is equal to the base bitwise weighted sum obtained by restoration of the deep judgment sequence in the mutation correction sequence included in the DNA sequence obtained by sequencing according to the same rule, the position is the base deletion position; inserting the base at the position and correcting the sequence to an unmutated preliminary data DNA sequence;

(4) restoring the unmutated preliminary data DNA sequences to data.

7. The method of claim 6, wherein the DNA sequences obtained by sequencing are a plurality of data DNA sequences, and the preliminary data DNA sequence of each data DNA sequence comprises an indexDNA sequence representing the position information of a data conversion unit and a dataDNA sequence representing the data content information of the data conversion unit, and the step (4) comprises:

(4-1) restoring the indexDNA sequence in each data DNA sequence to a ternary number sequence according to an indexDNA sequence conversion rule, and then restoring the ternary number sequence to a position number of the conversion unit in the data; wherein the indexDNA sequence conversion rule is:

(a) for the i-th position in the indexDNA sequence, the two bases before this position are represented as d=[i−2, i−1];

(b) for the first two positions in the indexDNA sequence, the corresponding conversion between ternary numbers and bases is performed according to the correspondence corresponding with the condition d∉Set {AT,CT,TT,CA,AA,CC,GG} shown in the table below;

| Conditions | Correspondence | |
| --- | --- | --- |
| | Ternary numbers | Bases |
| d = [A, T] | 0, 1, 2 | A, T, C |
| d = [C, T] | 0, 1, 2 | A, T, C |
| d = [T, T] | 0, 1, 2 | A, T, C |
| d = [A, A] | 0, 1, 2 | T, C, G |
| d = [G, G] | 0, 1, 2 | A, T, C |
| d ∈ Set{CC, GC, TC, AC} | 0, 1, 2 | T, C, G |
| d ∉ Set{AT, CT, TT, CA, AA, CC, GG} | 0, 1, 2 | G, A, T |

(c) starting from the third position in the indexDNA sequence, the conversion is conducted in turn according to the rules shown in the table above by: first, judging which condition in the table the i-th position satisfies, and then performing the corresponding conversion between the ternary number and the base at the i-th position according to the correspondence corresponding with the condition;

(4-2) restoring the dataDNA sequence in each data DNA sequence to data according to a dataDNA sequence conversion rule; wherein the dataDNA sequence conversion rule is:

(a) for the i-th position in the dataDNA sequence, the two bases before this position are represented as d=[i−2, i−1];

(b) for the first two positions in the dataDNA sequence, the corresponding conversion between binary numbers and bases is performed according to the correspondence corresponding with the condition d∉Set {AT, CT, TT, CA, AA, GG, CC} shown in the table below;

| Conditions | Correspondence | |
| --- | --- | --- |
| | Binary numbers | Bases |
| d = [A, T] | 0, 10, 11 | A, T, C |
| d = [C, T] | 0, 10, 11 | A, T, C |
| d = [T, T] | 0, 1 | A, C |
| d = [C, A]* | — | C |
| d = [A, A] | 0, 10, 11 | T, C, G |
| d = [G, G] | 0, 10, 11 | A, T, C |
| d = [C, C] | 0, 10, 11 | A, T, G |
| d ∉ Set{AT, CT, TT, CA, AA, GG, CC} | 00, 01, 10, 11 | A, T, C, G |

*wherein when d = [C, A], base C is at the i-th position, and the base C does not correspond to any binary number (c) starting from the third position in the dataDNA sequence, the conversion is conducted in turn according to the rules shown in the table above by: first, judging which condition in the table the i-th position satisfies, and then performing the corresponding conversion between the binary number and the base at the i-th position according to the correspondence corresponding with the condition;

(d) when the binary number sequence has only 1 or 2 positions left, the conversion between binary numbers and bases is performed using the rules shown in the table below;

| | Bases | | | | | |
| --- | --- | --- | --- | --- | --- | --- |
| | AC | TC | CG | GA | GT | GC |
| Binary number sequence | 0 | 1 | 00 | 01 | 10 | 11 |

(4-3) connecting the data restored from the dataDNA sequences of the respective data DNA sequences in the order of their position numbers, to obtain restored data.

8. The method of claim 7, wherein in step (4-2), the dataDNA sequence is restored to data in binary number form, or the data in binary number form is further restored to character strings; and the restored data in step (4-3) is the data in binary number form, or raw data further restored from the data in binary number form, or character string data obtained by connecting the character strings restored from the dataDNA sequence according to the order of their position numbers, or data further restored from the character string data.

9. A method for restoring encrypted DNA sequences obtained by sequencing to data, comprising:
(1) providing a user name and a password to obtain a corresponding mode between a specific binary number and a specific base in each set of correspondences in the dataDNA sequence conversion rule, wherein the corresponding mode is the one set for the same user name and password when data is converted into encrypted DNA sequences;
(2) restoring the encrypted DNA sequences obtained by sequencing to data using the method for correcting DNA sequence obtained by sequencing and restoring the same to data, the method comprising:
(2-1) providing DNA sequences obtained by sequencing, the DNA sequences comprising preliminary data DNA sequences and mutation correction sequences, wherein the preliminary data DNA sequence comprises data content information of a data conversion unit; wherein the preliminary data DNA sequence in the DNA sequence obtained by sequencing has at most one base mutation;
(2-2) based on each preliminary data DNA sequence, calculating a base number judgement value X'(i) of the preliminary data DNA sequence according the following formula $X'(i) = (-1)^{N(i)}$ wherein i=A, T, C, G; N(i) is the number of base i present in the preliminary data DNA sequence;
comparing the base number judgement value X'(i) of the preliminary data DNA sequence with the base judgement value X(i) obtained by restoration of the preliminary judgement sequence in the mutation correction sequence included in the DNA sequence obtained by sequencing according to the same rule
if the base number judgement values of two bases change, it indicates that the preliminary data DNA sequence has a base substitution compared to the unmutated preliminary data DNA sequence, and the substitution is a substitution of one of the two bases by the other;
if only the base number judgement value of base changes, it indicates that the preliminary data DNA sequence has insertion or deletion of this base compared to the unmutated preliminary data DNA sequence;
if none of the base number judgment values of base change, it indicates that the preliminary data DNA sequence has no mutation;
(2-3) based on the preliminary data DNA sequence, calculating a base bitwise weighted sum' of the preliminary data DNA sequence according to the following formula:

$$sum' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence;
comparing the base bitwise weighted sum' of the preliminary data DNA sequence with the base bitwise weighted sum obtained by restoration of the deep judgment sequence in the mutation correction sequence included in the DNA sequence obtained by sequencing according to the same rule;
in the case where the preliminary data DNA sequence has base substitution compared to the unmutated preliminary data DNA sequence: if sum'>sum, the base substitution is that the base having a smaller val(i) value is substituted by the base with a larger val(i) value; if sum'<sum, the base substitution is that the base having a larger val(i) value is substituted by the base with a smaller val(i) value; the position coordinate at which the base substitution occurs is the absolute value of the divisor obtained by dividing the difference between sum' and sum by the difference between the val(i) of the two bases; substituting the base at the position by the other of the two bases and correcting the sequence to an unmutated preliminary data DNA sequence;
in the case where the preliminary data DNA sequence has insertion or deletion of one base compared to the unmutated preliminary data DNA sequence;
if sum'>sum, it indicates that base insertion occurs, and the base insertion position is judged as follows: starting from the position where the base appears for the first time in the preliminary data DNA sequence, deleting the base at each position, and calculating a base bitwise weighted sum" of the preliminary data DNA sequence after deletion according to the following formula:

$$sum'' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are deleted;
when the base bitwise weighted sum" calculated after the base at a certain position is deleted is equal to the base bitwise weighted sum obtained by restoration of the deep judgment sequence in the mutation correction sequence included in the DNA sequence obtained by sequencing according to the same rule, the position is the base insertion position; deleting the base at the position and correcting the sequence to an unmutated preliminary data DNA sequence;
if sum'<sum, it indicates that base deletion occurs, and the base deletion position is judged as follows: starting from the first position of the preliminary data DNA sequence, inserting the base to each position, and calculating a base bitwise weighted sum''' of the preliminary data DNA sequence after insertion according to the following formula:

$$sum''' = \sum_{i=1}^{N} val(i) * position(i)$$

wherein i=A, T, C, G; val(i) is the value of base i, and val(A), val(T), val(C), val(G) correspond to 1, 2, 3, 4 respectively; position(i) is the position coordinate of the base i; N is the total length of the preliminary data DNA sequence after the bases are inserted;
when the base bitwise weighted sum''' calculated after the base is inserted at a certain position is equal to the base bitwise weighted sum obtained by restoration of the deep judgment sequence in the mutation correction sequence included in the DNA sequence obtained by sequencing according to the same rule, the position is the base deletion position; inserting the base at the position and correcting the sequence to an unmutated preliminary data DNA sequence;

(2-4) restoring the mutated preliminary DNA sequence to date;

wherein when the dataDNA sequence of each DNA sequence is restored to data according to the dataDNA sequence conversion rule, the specific base is restored to a corresponding specific binary number according to the corresponding mode generated in step (1).

10. The method of claim 6, wherein the method is implemented on a computer.

11. The method of claim 4, wherein step (2-1) comprises:

(2-1-1) converting the position number of the data conversion unit in the data into a ternary number sequence with a fixed number of bits, and then converting the ternary number sequence into an indexDNA sequence according to an indexDNA sequence conversion rule, where the number of bases of the indexDNA sequence is the same as the number of bits of the ternary number sequence;

wherein the indexDNA sequence conversion rule is:

(a) for the i-th position in the indexDNA sequence, the two bases before this position are represented as d=[i−2, i−1];

(b) for the first two positions in the indexDNA sequence, the corresponding conversion between ternary numbers and bases is performed according to the correspondence corresponding with the condition d E Set {AT, CT,TT,CA,AA,CC,GG} shown in the table below;

|  | Correspondence | |
| --- | --- | --- |
| Conditions | Ternary numbers | Bases |
| d = [A, T] | 0, 1, 2 | A, T, C |
| d = [C, T] | 0, 1, 2 | A, T, C |
| d = [T, T] | 0, 1, 2 | A, T, C |
| d = [A, A] | 0, 1, 2 | T, C, G |
| d = [G, G] | 0, 1, 2 | A, T, C |
| d∈Set{CC, GC, TC, AC} | 0, 1, 2 | T, C, G |
| d∉Set{AT, CT, TT, CA, AA, CC, GG} | 0, 1, 2 | G, A, T |

(c) starting from the third position in the indexDNA sequence, the conversion is conducted in turn according to the rules shown in the table above by: first, judging which condition in the table the i-th position satisfies, and then performing the corresponding conversion between the ternary number and the base at the i-th position according to the correspondence corresponding with the condition;

(2-1-2) converting the binary number sequence of the data conversion unit into a dataDNA sequence according to a dataDNA sequence conversion rule;

wherein the dataDNA sequence conversion rule is:

(a) for the i-th position in the dataDNA sequence, the two bases before this position are represented as d=[i−2, i−1];

(b) for the first two positions in the dataDNA sequence, the corresponding conversion between binary numbers and bases is performed according to the correspondence corresponding with the condition d∉Set {AT, CT, TT, CA, AA, GG, CC} shown in the table below;

|  | Correspondence | |
| --- | --- | --- |
| Conditions | Binary numbers | Bases |
| d = [A, T] | 0, 10, 11 | A, T, C |
| d = [C, T] | 0, 10, 11 | A, T, C |
| d = [T, T] | 0, 1 | A, C |
| d = [C, A]* | — | C |
| d = [A, A] | 0, 10, 11 | T, C, G |
| d = [G, G] | 0, 10, 11 | A, T, C |
| d = [C, C] | 0, 10, 11 | A, T, G |
| d ∉ Set{AT, CT, TT, CA, AA, GG, CC} | 00, 01, 10, 11 | A, T, C, G |

*wherein when d = [C, A], base C is at the i-th position, and the base C does not correspond to any binary number (c) starting from the third position in the dataDNA sequence, the conversion is conducted in turn according to the rules shown in the table above by: first, judging which condition in the table the i-th position satisfies, and then performing the corresponding conversion between the binary number and the base at the i-th position according to the correspondence corresponding with the condition;

(d) when the binary number sequence has only 1 or 2 positions left, the conversion between binary numbers and bases is performed using the rules shown in the table below;

|  | Bases | | | | | |
| --- | --- | --- | --- | --- | --- | --- |
|  | AC | TC | CG | GA | GT | GC |
| Binary number sequence | 0 | 1 | 00 | 01 | 10 | 11 |

(2-1-3) connecting the indexDNA sequence and the dataDNA sequence of the data conversion unit, and adding a protection sequence of 2 bases in length at the junction to obtain an index+dataDNA sequence as the preliminary data DNA sequence without a mutation correction sequence.

12. The method of claim 11, wherein in step (2-1-3), the correctionDNA is connected to one end of the dataDNA in the index+dataDNA sequence.

13. The method of claim 2, wherein the method is implemented on a computer.

14. The method of claim 4, wherein the method is implemented on a computer.

15. The method of claim 11, wherein the method is implemented on a computer.

16. The method of claim 9, wherein the DNA sequences obtained by sequencing are a plurality of data DNA sequences, and the preliminary data DNA sequence of each data DNA sequence comprises an indexDNA sequence representing the position information of a data conversion unit and a dataDNA sequence representing the data content information of the data conversion unit, and the step (2-4) comprises:

(2-4-1) restoring the indexDNA sequence in each data DNA sequence to a ternary number sequence according to an indexDNA sequence conversion rule, and then restoring the ternary number sequence to a position number of the conversion unit in the data; wherein the indexDNA sequence conversion rule is:

(a) for the i-th position in the indexDNA sequence, the two bases before this position are represented as d=[i−2, i−1];

(b) for the first two positions in the indexDNA sequence, the corresponding conversion between ternary numbers and bases is performed according to the correspondence corresponding with the condition d∉Set {AT,CT, TT,CA,AA,CC,GG} shown in the table below;

|  | Correspondence | |
|---|---|---|
| Conditions | Ternary numbers | Bases |
| d = [A, T] | 0, 1, 2 | A, T, C |
| d = [C, T] | 0, 1, 2 | A, T, C |
| d = [T, T] | 0, 1, 2 | A, T, C |
| d = [A, A] | 0, 1, 2 | T, C, G |
| d = [G, G] | 0, 1, 2 | A, T, C |
| d ∈ Set{CC, GC, TC, AC} | 0, 1, 2 | T, C, G |
| d ∉ Set{AT, CT, TT, CA, AA, CC, GG} | 0, 1, 2 | G, A, T |

(c) starting from the third position in the indexDNA sequence, the conversion is conducted in turn according to the rules shown in the table above by: first, judging which condition in the table the i-th position satisfies, and then performing the corresponding conversion between the ternary number and the base at the i-th position according to the correspondence corresponding with the condition;

(2-4-2) restoring the dataDNA sequence in each data DNA sequence to data according to a dataDNA sequence conversion rule; wherein the dataDNA sequence conversion rule is:

(a) for the i-th position in the dataDNA sequence, the two bases before this position are represented as d=[i−2, i−1];

(b) for the first two positions in the dataDNA sequence, the corresponding conversion between binary numbers and bases is performed according to the correspondence corresponding with the condition d∉Set {AT, CT, TT, CA, AA, GG, CC} shown in the table below;

|  | Correspondence | |
|---|---|---|
| Conditions | Binary numbers | Bases |
| d = [A, T] | 0, 10, 11 | A, T, C |
| d = [C, T] | 0, 10, 11 | A, T, C |
| d = [T, T] | 0, 1 | A, C |
| d = [C, A]* | — | C |
| d = [A, A] | 0, 10, 11 | T, C, G |
| d = [G, G] | 0, 10, 11 | A, T, C |
| d = [C, C] | 0, 10, 11 | A, T, G |
| d ∉ Set{AT, CT, TT, CA, AA, GG, CC} | 00, 01, 10, 11 | A, T, C, G |

*wherein when d = [C, A], base C is at the i-th position, and the base C does not correspond to any binary number (c) starting from the third position in the dataDNA sequence, the conversion is conducted in turn according to the rules shown in the table above by: first, judging which condition in the table the i-th position satisfies, and then performing the corresponding conversion between the binary number and the base at the i-th position according to the correspondence corresponding with the condition;

(d) when the binary number sequence has only 1 or 2 positions left, the conversion between binary numbers and bases is performed using the rules shown in the table below;

|  | Bases | | | | | |
|---|---|---|---|---|---|---|
|  | AC | TC | CG | GA | GT | GC |
| Binary number sequence | 0 | 1 | 00 | 01 | 10 | 11 |

(2-4-3) connecting the data restored from the dataDNA sequences of the respective data DNA sequences in the order of their position numbers, to obtain restored data.

17. The method of claim 16, wherein in step (2-4-2), the dataDNA sequence is restored to data in binary number form, or the data in binary number form is further restored to character strings; and the restored data in step (2-4-3) is the data in binary number form, or raw data further restored from the data in binary number form, or character string data obtained by connecting the character strings restored from the dataDNA sequence according to the order of their position numbers, or data further restored from the character string data.

18. The method of claim 7, wherein the method is implemented on a computer.

19. The method of claim 9, wherein the method is implemented on a computer.

20. The method of claim 16, wherein the method is implemented on a computer.

* * * * *

SEQUENCE LISTING

<160> NUMBER OF SEQ ID NOS: 45

<210> SEQ ID NO 1
<211> LENGTH: 16
<212> TYPE: DNA
<213> ORGANISM: Artificial Sequence
<220> FEATURE:
<223> OTHER INFORMATION: sequence example

<400> SEQUENCE: 1
atgcttcgac gtcgag                                                       16

<210> SEQ ID NO 2
<211> LENGTH: 10
<212> TYPE: DNA
<213> ORGANISM: Artificial Sequence
<220> FEATURE:
<223> OTHER INFORMATION: deep judgment sequence

<400> SEQUENCE: 2
ggcgaatcct                                                              10

<210> SEQ ID NO 3
<211> LENGTH: 15
<212> TYPE: DNA
<213> ORGANISM: Artificial Sequence
<220> FEATURE:
<223> OTHER INFORMATION: correctionDNA sequence

<400> SEQUENCE: 3
cggccggcga atcct                                                        15

<210> SEQ ID NO 4
<211> LENGTH: 33
<212> TYPE: DNA
<213> ORGANISM: Artificial Sequence
<220> FEATURE:
<223> OTHER INFORMATION: stored sequence

<400> SEQUENCE: 4
atgcttcgac gtcgaggccg gccggcgaat cct                                    33

<210> SEQ ID NO 5
<211> LENGTH: 33
<212> TYPE: DNA
<213> ORGANISM: Artificial Sequence
<220> FEATURE:
<223> OTHER INFORMATION: mutated sequence

<400> SEQUENCE: 5
atccttcgac gtcgaggccg gccggcgaat cct                                    33

<210> SEQ ID NO 6
<211> LENGTH: 34
<212> TYPE: DNA
<213> ORGANISM: Artificial Sequence
<220> FEATURE:
<223> OTHER INFORMATION: mutated sequence

<400> SEQUENCE: 6
atgctatcga cgtcgaggcc ggccggcgaa tcct                                   34

<210> SEQ ID NO 7
<211> LENGTH: 32
<212> TYPE: DNA
<213> ORGANISM: Artificial Sequence -continued

```
<220> FEATURE:
<223> OTHER INFORMATION: mutated sequence

<400> SEQUENCE: 7
atgcttgacg tcgaggccgg ccggcgaatc ct                                  32

<210> SEQ ID NO 8
<211> LENGTH: 43
<212> TYPE: DNA
<213> ORGANISM: Artificial Sequence
<220> FEATURE:
<223> OTHER INFORMATION: dataDNA Sequence

<400> SEQUENCE: 8 tataccaccac gaagccacct aattagagaa gcaccaccac tac                     43

<210> SEQ ID NO 9
<211> LENGTH: 88
<212> TYPE: DNA
<213> ORGANISM: Artificial Sequence
<220> FEATURE:
<223> OTHER INFORMATION: dataDNA Sequence

<400> SEQUENCE: 9
tatacctagc tcctagcgcg aggtcacgcc gcactacaca ccttcgtgtc cacggagtct    60
aggatagctc ctaggactcc acctatac                                       88

<210> SEQ ID NO 10
<211> LENGTH: 77
<212> TYPE: DNA
<213> ORGANISM: Artificial Sequence
<220> FEATURE:
<223> OTHER INFORMATION: dataDNA Sequence

<400> SEQUENCE: 10
tataccacgg cacgcgcgcc acgtattacg gacttcacgc acgtaattcc acgctagcac    60
tccacggtca ccactac                                                   77

<210> SEQ ID NO 11
<211> LENGTH: 78
<212> TYPE: DNA
<213> ORGANISM: Artificial Sequence
<220> FEATURE:
<223> OTHER INFORMATION: dataDNA Sequence

<400> SEQUENCE: 11
tataccacgg cacgcgcgcc acgtattacg gacttcacgc acgtaattaa cgtagcggct    60
tagtggttcg gttacagt                                                  78

<210> SEQ ID NO 12
<211> LENGTH: 54
<212> TYPE: DNA
<213> ORGANISM: Artificial Sequence
<220> FEATURE:
<223> OTHER INFORMATION: dataDNA Sequence

<400> SEQUENCE: 12
tgcgtggagt gtacacgatt ctcgccttcg aacacacact ctagtgtgcg cctc          54

<210> SEQ ID NO 13
<211> LENGTH: 53
<212> TYPE: DNA
<213> ORGANISM: Artificial Sequence
<220> FEATURE:
```

```
<223> OTHER INFORMATION: dataDNA Sequence

<400> SEQUENCE: 13
gattagaaga gagctcacct tagtgttaat cctccacgaa ccgagattat tga        53

<210> SEQ ID NO 14
<211> LENGTH: 57
<212> TYPE: DNA
<213> ORGANISM: Artificial Sequence
<220> FEATURE:
<223> OTHER INFORMATION: dataDNA Sequence

<400> SEQUENCE: 14
gtcttcgaga cacttcactc ggtctacctt aatcacacac gttattcacc tatccga    57

<210> SEQ ID NO 15
<211> LENGTH: 62
<212> TYPE: DNA
<213> ORGANISM: Artificial Sequence
<220> FEATURE:
<223> OTHER INFORMATION: dataDNA Sequence

<400> SEQUENCE: 15
gcaccacctt ccaccactcc acttagtaca cacctattcc gttaccactc cacctcctca  60
tc                                                                62

<210> SEQ ID NO 16
<211> LENGTH: 15
<212> TYPE: DNA
<213> ORGANISM: Artificial Sequence
<220> FEATURE:
<223> OTHER INFORMATION: IndexDNA

<400> SEQUENCE: 16
ggcggcggcg gcggc                                                  15

<210> SEQ ID NO 17
<211> LENGTH: 22
<212> TYPE: DNA
<213> ORGANISM: Artificial Sequence
<220> FEATURE:
<223> OTHER INFORMATION: DataDNA

<400> SEQUENCE: 17
atcgatcgat cgatcgatcg at                                          22

<210> SEQ ID NO 18
<211> LENGTH: 15
<212> TYPE: DNA
<213> ORGANISM: Artificial Sequence
<220> FEATURE:
<223> OTHER INFORMATION: CorrectionDNA

<400> SEQUENCE: 18
gtggagatcg ccggc                                                  15

<210> SEQ ID NO 19
<211> LENGTH: 115
<212> TYPE: DNA
<213> ORGANISM: Artificial Sequence
<220> FEATURE:
<223> OTHER INFORMATION: example sequence in Figure 11

<400> SEQUENCE: 19
ggcggcggcg gcggcagtcg gaggccgatt aaccttccgt gatattataa ttacggctta  60
```

```
gaggtgtagt tacaccgcac acacgcgcca cttcttacca cgctaggagg ccgcg        115
```

<210> SEQ ID NO 20
<211> LENGTH: 113
<212> TYPE: DNA
<213> ORGANISM: Artificial Sequence
<220> FEATURE:
<223> OTHER INFORMATION: example sequence in Figure 11

<400> SEQUENCE: 20

```
ggcggcggcg gcggtgctct ctccacggcg gacttatcac gagatagtgg cttactcacc    60
ggcacgtggc tcacacgccg tcactattac tagaacctcg cttactcggg ccg          113
```

<210> SEQ ID NO 21
<211> LENGTH: 119
<212> TYPE: DNA
<213> ORGANISM: Artificial Sequence
<220> FEATURE:
<223> OTHER INFORMATION: example sequence in Figure 11

<400> SEQUENCE: 21

```
ggcggcggcg gcggaacacc ggaaggccac taagtcttca cacactattc taccttctta    60 tattcacgt ggacttatat tacttcttcc gcacacgtaa tacacgctag gcgctcccg     119
```

<210> SEQ ID NO 22
<211> LENGTH: 117
<212> TYPE: DNA
<213> ORGANISM: Artificial Sequence
<220> FEATURE:
<223> OTHER INFORMATION: example sequence in Figure 11

<400> SEQUENCE: 22

```
ggcggcggcg gcgcgtacgt gagccgtagg cacacgtatc cacacacacc gagtgtccac    60
taagaacttc gttccacgca cgtggaagag attcacacgt aacgctacgt ggtgggg     117
```

<210> SEQ ID NO 23
<211> LENGTH: 117
<212> TYPE: DNA
<213> ORGANISM: Artificial Sequence
<220> FEATURE:
<223> OTHER INFORMATION: example sequence in Figure 11

<400> SEQUENCE: 23

```
ggcggcggcg gcgccgttcg ctcgcttacc acgtgatatt atattacggc ttagaaggtg    60
taccacactt ctagtataca ccaccgcaca cgtaataccg agtgctagga ggacggc     117
```

<210> SEQ ID NO 24
<211> LENGTH: 118
<212> TYPE: DNA
<213> ORGANISM: Artificial Sequence
<220> FEATURE:
<223> OTHER INFORMATION: example sequence in Figure 11

<400> SEQUENCE: 24

```
ggcggcggcg gcgctataca cttattcttc cgcgattcac tattcgcgct accactacga    60
cacacacgat aagtggaact accactcaca cactaggtca caacgcttac ctctgcgg    118
```

<210> SEQ ID NO 25
<211> LENGTH: 123
<212> TYPE: DNA
<213> ORGANISM: Artificial Sequence
<220> FEATURE:

```
<223> OTHER INFORMATION: example sequence in Figure 11

<400> SEQUENCE: 25
ggcggcggcg gcgtgagtct tcacttcttt acggtcacga atattcacta caccactata    60
cacgcggtga tagttccact acacacacac ttcacaccgc ttacgccgcg tgcctcctcc   120
gcg                                                                 123

<210> SEQ ID NO 26
<211> LENGTH: 120
<212> TYPE: DNA
<213> ORGANISM: Artificial Sequence
<220> FEATURE:
<223> OTHER INFORMATION: example sequence in Figure 11

<400> SEQUENCE: 26
ggcggcggcg gcgtcaccac accacttaac tagggctcgt tagatagtca ctaggctcgt    60
cttaatcacc acttcttcct aagaacttcg ttccacactt acgccggtgg ctagttcgcc   120

<210> SEQ ID NO 27
<211> LENGTH: 117
<212> TYPE: DNA
<213> ORGANISM: Artificial Sequence
<220> FEATURE:
<223> OTHER INFORMATION: example sequence in Figure 11

<400> SEQUENCE: 27
ggcggcggcg gcgttataca cttccgccac gcgataccac ttatccacac accggttcgg    60
cacgatagcc gtctcactta tatctcgaag gcctccgtac aacgctattg tgtgcgc      117

<210> SEQ ID NO 28
<211> LENGTH: 116
<212> TYPE: DNA
<213> ORGANISM: Artificial Sequence
<220> FEATURE:
<223> OTHER INFORMATION: example sequence in Figure 11

<400> SEQUENCE: 28
ggcggcggcg gccggaccac accaccacat tctcaccacg ttcgttcgtc cgttctcgaa    60
ggaaggtgga agaagagaga tagaagatta ggcacactta gcgcatgttc tcgcgg       116

<210> SEQ ID NO 29
<211> LENGTH: 114
<212> TYPE: DNA
<213> ORGANISM: Artificial Sequence
<220> FEATURE:
<223> OTHER INFORMATION: example sequence in Figure 11

<400> SEQUENCE: 29
ggcggcggcg gccgcaaggc taatcacctg gatatagcca cgccacgcca ctcgatacac    60
ttatcggtta gtcttctcac taagaacttc gttatcgcgt gcttagtcct gcgc         114

<210> SEQ ID NO 30
<211> LENGTH: 118
<212> TYPE: DNA
<213> ORGANISM: Artificial Sequence
<220> FEATURE:
<223> OTHER INFORMATION: example sequence in Figure 11

<400> SEQUENCE: 30
ggcggcggcg gccgtataca cttccgccac gccacgcgat acacttatcg gtcttaatca    60
ccacttctcg gtaggcgata gttatcgctt atacacttcc gccggtagag cgccgccg    118
```

<210> SEQ ID NO 31
<211> LENGTH: 117
<212> TYPE: DNA
<213> ORGANISM: Artificial Sequence
<220> FEATURE:
<223> OTHER INFORMATION: example sequence in Figure 11

<400> SEQUENCE: 31
ggcggcggcg gcctcataca cttattccac acttatcgag taggcttagt agatagccgt    60
ctcacttata tctctcctta gacgcttctt cttaggccac tgtgctattc ttagggc      117

<210> SEQ ID NO 32
<211> LENGTH: 118
<212> TYPE: DNA
<213> ORGANISM: Artificial Sequence
<220> FEATURE:
<223> OTHER INFORMATION: example sequence in Figure 11

<400> SEQUENCE: 32
ggcggcggcg gccttagtag cggtgatagt tccacaccac ctgtggttcg tacgttcgac    60
cggctactta tatagcacac taggccacgt tcaccactta ccacgtggcg cgtgcccg     118

<210> SEQ ID NO 33
<211> LENGTH: 119
<212> TYPE: DNA
<213> ORGANISM: Artificial Sequence
<220> FEATURE:
<223> OTHER INFORMATION: example sequence in Figure 11

<400> SEQUENCE: 33
ggcggcggcg gcctagacac ttaagacgta ggcttcgttc acgttacacc gcttataatt    60
cacggccacg ttcaccactt accacgtgat cacgctcgag tcaacgtgga ggcgggcgg   119

<210> SEQ ID NO 34
<211> LENGTH: 121
<212> TYPE: DNA
<213> ORGANISM: Artificial Sequence
<220> FEATURE:
<223> OTHER INFORMATION: example sequence in Figure 11

<400> SEQUENCE: 34
ggcggcggcg gccaggagga tacggctact tatacaccac cacgccactt ccacgcttat    60
aattctatac cgcttataat tcactactta ccacggccga ttaacacgct attactaggc   120
g                                                                  121

<210> SEQ ID NO 35
<211> LENGTH: 120
<212> TYPE: DNA
<213> ORGANISM: Artificial Sequence
<220> FEATURE:
<223> OTHER INFORMATION: example sequence in Figure 11

<400> SEQUENCE: 35
ggcggcggcg gccacagaag cggtcacttc acgcacgtaa ttatcttctc ttcacgctcc    60
tcgcggcaca cgtaagattc acacaccact taggccacta atacacgtgg ctctaggccg   120

<210> SEQ ID NO 36
<211> LENGTH: 114
<212> TYPE: DNA
<213> ORGANISM: Artificial Sequence
<220> FEATURE:

<223> OTHER INFORMATION: example sequence in Figure 11

<400> SEQUENCE: 36
ggcggcggcg gccatagtat agttccacga cgtacacgtt acacacgctc cgcacgacac    60
tctacttacc acgtaggctt agtagatagc taggctacgt gcttaggatc gccc         114

<210> SEQ ID NO 37
<211> LENGTH: 112
<212> TYPE: DNA
<213> ORGANISM: Artificial Sequence
<220> FEATURE:
<223> OTHER INFORMATION: example sequence in Figure 11

<400> SEQUENCE: 37
ggcggcggcg gctcggcgat cacgatagat aattcggcac acgaagatag catagttatt    60
aacggaagag ttatattata ttcggcgtgg ccggcgcggc ttagtggtgc gg           112

<210> SEQ ID NO 38
<211> LENGTH: 111
<212> TYPE: DNA
<213> ORGANISM: Artificial Sequence
<220> FEATURE:
<223> OTHER INFORMATION: example sequence in Figure 11

<400> SEQUENCE: 38
ggcggcggcg gctccgacgg ccacacactc gctctagtgc gctagttatt aaccgaagag    60
ttatattata ttcggcgtgg taggcttagc tcacgtcgct tcctacgcgc c            111

<210> SEQ ID NO 39
<211> LENGTH: 116
<212> TYPE: DNA
<213> ORGANISM: Artificial Sequence
<220> FEATURE:
<223> OTHER INFORMATION: example sequence in Figure 11

<400> SEQUENCE: 39
ggcggcggcg gctctgaagt aattaatata acgccacgcc acgccacgcc acgccacgcc    60
acgtggtagg cttagctcac ggttagtaat cgagattaat gagctattgg cggccg       116

<210> SEQ ID NO 40
<211> LENGTH: 119
<212> TYPE: DNA
<213> ORGANISM: Artificial Sequence
<220> FEATURE:
<223> OTHER INFORMATION: example sequence in Figure 11

<400> SEQUENCE: 40
ggcggcggcg gcttggttcg ctcgctcact tatcacgatt tataggcttc gttcgacacg    60
atccttaggc cactaatacc ttccacttcc acggcactaa gattcgtggc cacctcgcc   119

<210> SEQ ID NO 41
<211> LENGTH: 116
<212> TYPE: DNA
<213> ORGANISM: Artificial Sequence
<220> FEATURE:
<223> OTHER INFORMATION: example sequence in Figure 11

<400> SEQUENCE: 41
ggcggcggcg gcttcgccgt aggcacacac caccgtggtt ccgtacgttc gaccggctac    60
ttatatagca cactatcctt accacgacac ttaagacgta gcgcttatag tcgccc       116

```
<210> SEQ ID NO 42
<211> LENGTH: 114
<212> TYPE: DNA
<213> ORGANISM: Artificial Sequence
<220> FEATURE:
<223> OTHER INFORMATION: example sequence in Figure 11

<400> SEQUENCE: 42
ggcggcggcg gcttagacac gagcacgtta caccgcttat aattcactac ttaccacggc     60
cgatagacgt gtgaacgtta tccgtaacac acgcgcggga gctaggagga cccg          114

<210> SEQ ID NO 43
<211> LENGTH: 113
<212> TYPE: DNA
<213> ORGANISM: Artificial Sequence
<220> FEATURE:
<223> OTHER INFORMATION: example sequence in Figure 11

<400> SEQUENCE: 43
ggcggcggcg gctagacaca cttacgccgg cttatactct agacgtgagc cgtaggcaca     60
cacacggtta agccgcgtgt ggcctccaca cgtagtagag ctatcctacg cgg           113

<210> SEQ ID NO 44
<211> LENGTH: 115
<212> TYPE: DNA
<213> ORGANISM: Artificial Sequence
<220> FEATURE:
<223> OTHER INFORMATION: example sequence in Figure 11

<400> SEQUENCE: 44
ggcggcggcg gctacattca ctactccacc taattattac gttaactcga tcaccaccgc     60
cacgacacta agttagatct taatcttaac acgtccgccg tgcttgccat ccccc         115

<210> SEQ ID NO 45
<211> LENGTH: 117
<212> TYPE: DNA
<213> ORGANISM: Artificial Sequence
<220> FEATURE:
<223> OTHER INFORMATION: example sequence in Figure 11

<400> SEQUENCE: 45
ggcggcggcg gctattccga cacttctcca ccgatagcca tgcctccggc cacacttccg     60
caccactcga tcacacctac accgactaat cgcactacgt cacgtggcgg cgggccc      117
```